(12) United States Patent
Salathia et al.

(10) Patent No.: US 10,975,371 B2
(45) Date of Patent: Apr. 13, 2021

(54) NUCLEIC ACID SEQUENCE ANALYSIS FROM SINGLE CELLS

(71) Applicant: ILLUMINA, INC., San Diego, CA (US)

(72) Inventors: Neeraj Salathia, San Diego, CA (US); Jian-Bing Fan, San Diego, CA (US); Fiona Kaper, San Diego, CA (US); Gordon M. Cann, San Diego, CA (US); Arash Jamshidi, San Diego, CA (US); Alex Aravanis, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 670 days.

(21) Appl. No.: 14/855,207

(22) Filed: Sep. 15, 2015

(65) Prior Publication Data

US 2016/0053253 A1 Feb. 25, 2016

Related U.S. Application Data

(63) Continuation-in-part of application No. PCT/US2015/028062, filed on Apr. 28, 2015.

(60) Provisional application No. 62/211,597, filed on Aug. 28, 2015, provisional application No. 61/987,433, filed on May 1, 2014, provisional application No. 61/985,983, filed on Apr. 29, 2014.

(51) Int. Cl.
*C12N 15/10* (2006.01)
*C12Q 1/6869* (2018.01)
*C12Q 1/6853* (2018.01)
*C12Q 1/6806* (2018.01)

(52) U.S. Cl.
CPC ..... *C12N 15/1065* (2013.01); *C12N 15/1093* (2013.01); *C12N 15/1096* (2013.01); *C12Q 1/6806* (2013.01); *C12Q 1/6853* (2013.01); *C12Q 1/6869* (2013.01); *C12Q 2525/155* (2013.01); *C12Q 2525/161* (2013.01); *C12Q 2525/179* (2013.01); *C12Q 2525/191* (2013.01); *C12Q 2563/159* (2013.01); *C12Q 2563/179* (2013.01)

(58) Field of Classification Search
CPC ............ C12N 15/1065; C12N 15/1096; C12Q 1/686; C12Q 1/6869; C12Q 1/6853
See application file for complete search history.

(56) References Cited

U.S. PATENT DOCUMENTS

| 6,277,607 B1 * | 8/2001 | Tyagi | C12Q 1/6818 435/5 |
| 2004/0110201 A1 * | 6/2004 | Rashtchian | C12N 15/1096 435/6.11 |
| 2010/0120098 A1 * | 5/2010 | Grunenwald | C12N 15/10 435/91.2 |
| 2012/0010091 A1 | 1/2012 | Linnarson | |
| 2015/0329891 A1 * | 11/2015 | Tan | C12Q 1/6804 435/91.1 |
| 2016/0122753 A1 * | 5/2016 | Mikkelsen | C12Q 1/6844 506/4 |

FOREIGN PATENT DOCUMENTS

| JP | 2007-525963 A | 9/2007 | |
| WO | 2010117620 A2 | 10/2010 | |
| WO | WO-2012058488 A9 * | 7/2012 | ........... C12Q 1/6832 |
| WO | 2014047561 A1 | 3/2014 | |
| WO | 2015031691 A1 | 3/2015 | |
| WO | 2015103339 A1 | 7/2015 | |
| WO | 2015168161 | 11/2015 | |

OTHER PUBLICATIONS

Nextera® XT DNA Sample Preparation Guide, Oct. 2012, pp. 1-48 (Year: 2012).*
Horn-Saban et al. Encyclopedia of Analytical Chemistry (2011) John Wiley & Sons, Ltd., pp. 1-30. (Year: 2011).*
International Search Report and Written Opinion dated Dec. 14, 2016 in PCT/US2016/049046.
Evan Z. Macosko et al: "Highly Parallel Genome-wide Expression Profiling of Individual Cells Using Nanoliter Droplets", Cell, vol. 161, No. 5, May 1, 2015 (May 1, 2015), pp. 1202-1214, XP055323004.
Sarah Lamble et al: "Improved workflows for high throughput library preparation using the transposome-based nextera system", BMC Biotechnology, vol. 13, No. 1, Jan. 1, 2013 (Jan. 1, 2013), p. 104, XP055245099.
Adey, et al., "Rapid, low-input, low-bias construction of shotgun fragment libraries by high-density in vitro transposition", Genome Biology vol. 11(12), 2010, R119.
Brouilette, Scott et al., "A Simple and Novel Method for RNA-seq Library Preparation of Single Cell cDNA Analysis by Hyperactive Tn5 Transposase", Developmental Dynamics, 21 (10), 2012, 1584-1590.
Gertz, Jason et al., "Transposease mediated construction of RNA-seq libraries", Genome Research, 22 (1), 2012, 134-141.
Isalm, et al., "Quantitative single-cell RNA-seq with unique molecular identifiers", Nature Methods, 11(2), 2014, 163-166.
Picelli, Simone et al., "Full-length RNA-seq from single cells using Smart-seq2", Nature Protocols, 9(1), 2014, 171-181.
Saiful, Islam et al., "Characterization of the single-cell transcriptional landscape by high multiplex RNA-seq", Genome Research, vol. 21, No. 7, Jul. 7, 2011, 1160-1167.
Saiful, Islam et al., "Highly multiplexed and strand-specific single-cell RNA 5' end sequencing", Nature Protocols, Nature Publishing Group, May 1, 2012, 813-828.
Office Action dated Oct. 18, 2017 from related Japanese Application No. 2016-565421.
Illumina Bio-Rad SureCell WTA 3"Library Prep: Reference Guide. Document #1000000021452v01, Jun. 2017.

(Continued)

*Primary Examiner* — Angela M. Bertagna
(74) *Attorney, Agent, or Firm* — McNeill Baur PLLC

(57) ABSTRACT

Presented herein are methods and compositions for multiplexed single cell gene expression analysis. Some methods and compositions include the use of droplets and/or beads bearing unique barcodes such as unique molecular barcodes (UMI).

38 Claims, 22 Drawing Sheets
Specification includes a Sequence Listing.

(56) References Cited

OTHER PUBLICATIONS

The Scientist, "Illumina Bio-Rad Single-Cell Sequencing Solution", Published Apr. 9, 2017, downloaded on Dec. 20, 2019.
Extended European Search Report, European Application No. 20154378.2, dated Apr. 20, 2020, 8 pages.
Communication pursuant to Article 94(3), European Patent Office Application No. 16760336.4, dated Jul. 20, 2020, 5 pages.
Fan et al., "Highly Parallel Genome-Wide Expression Analysis of Single Mammalian Cells", PLOS One, vol. 7, No. 2, 2012, pp. 1-8.
Fan et al., "Single-cell RNA-seq transcriptome analysis of linear and circular RNAs in mouse preimplantation embryos", Genome Biology, 2015, 16:148, pp. 1-17.
Official Action (English translation), Japanese Patent Office, Japanese Patent Application No. 2016-565421, dated Oct. 23, 2017.

\* cited by examiner

Key sequence metrics using *100 pg HBR*

| Sequence Metric | | High Throughput GEx | Statistics STRT | | SMART |
|---|---|---|---|---|---|
| | | | Oligo-dT | Oligo-dT + Randomer | Oligo-dT |
| 1st Strand priming method | | Oligo-dT | Oligo-dT | | |
| Mapping rate | Aligned to Hg19 transcriptome | 63% | 75% | 50% | 78% |
| | Ribosomal | 1% | 2% | 12% | 1% |
| | Mitochondrial | 15% | 14% | 15% | 12% |
| | Other | 1% | 0% | 0% | 1% |
| | Unaligned | 20% | 9% | 23% | 8% |
| Correlation of gene-expression between technical replicates (r) | | 0.9 | 0.85 | 0.72 | 0.94 |
| No. of genes detected (FPKM>1) | | 10,021 | 11,254 | 11,683 | 8,492 |

Fig. 6

*Initial data from single cells*

| Sequence Metric | | High Througput GEx | | STRT | |
|---|---|---|---|---|---|
| | | | | | |
| 1st Strand priming method | | Oligo-dT | Oligo-dT | Oligo-dT | Oligo-dT + Randomer |
| Nextera version | | V2.B15 | V2.B15/V2.A14 | V2.B15/V2.A14 | V2.B15/V2.A14 |
| Mapping rate | Aligned to hg19 / mm10 | 69% | 77% | | 80% |
| | Ribosomal | 1% | 1% | | 5% |
| | Mitochondria | — | — | | — |
| | Other | 1% | 1% | | 0% |
| | Unaligned | 29% | 21% | | 14% |
| Correlation of gene-expression between technical replicates (r) | | 0.95 | 0.94 | | 0.60* |
| No. of genes detected (FPKM>1) | | 6,904 | 7,789 | | 8,727 |

\* Unusually low correlation due to one outlier.

Fig. 7 cDNA from single nuclei
*Overview of Fluidigm's C1 system for RNA-seq*

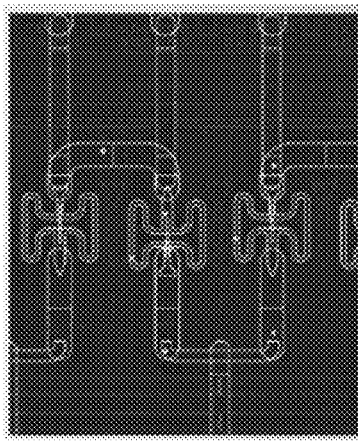
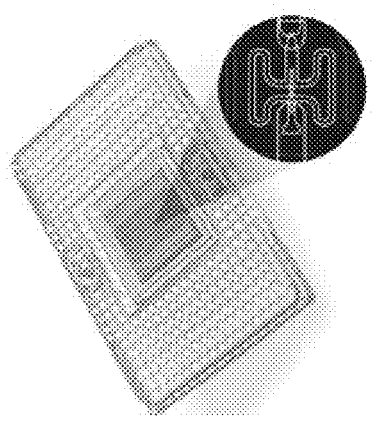
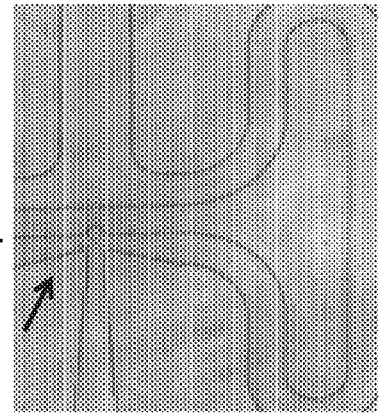

➢ Transcriptome profiling from nuclei rather than whole neurons
  ➢ Technically difficult to isolate neurons in high throughput
  ➢ RNA contamination from neighboring neuronal synaptic RNA ➢ C1 system designed for 96 nano-liter reaction volumes
  ➢ Nuclei loading and capture
  ➢ Wash, lysis
  ➢ cDNA synthesis
  ➢ PCR Amplification
  ➢ cDNA Harvest

Figure 14

Overview of RNA-seq using "Template switching" approach

➤ Polyadenylated RNA

RNA　　Poly A tail
wwwwwwAAAAAAAAAAAAAAAA

➤ Priming with tagged oligodT primer wwwwwwAAAAAAAAAAAAAAAA
　　　　TTTTTTTTTTTTTT ─────▶
　　　　　　　　　　　　　PCR primer binding site ➤ Template switching TS primer
　　　rGrGrG
　　　c c c
wwwwwwAAAAAAAAAAAAAAAA
　　　　TTTTTTTTTTTTTT ➤ Amplify cDNA ➤ Nextera Tagmentation ➤ Sequence

Figure 15

Advantages of SMART-plus
- Assay performance has been validated on a dataset compiled from >1,000 high quality single nuclei (A)
- Enhanced representation of 5' regions of gene-bodies (B)
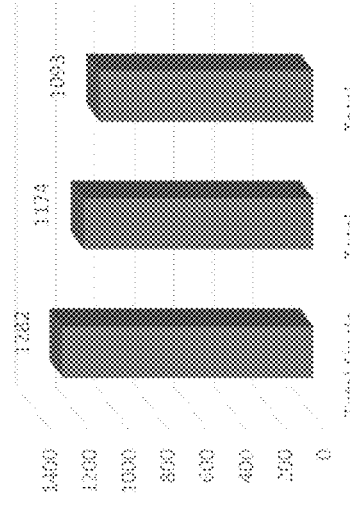
(A)
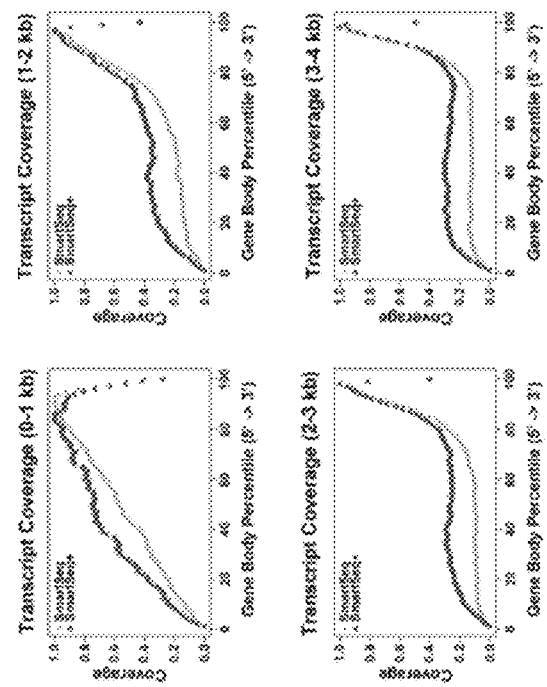
(B)
Figure 17

NUCLEIC ACID SEQUENCE ANALYSIS FROM SINGLE CELLS

RELATED APPLICATIONS

This application claims priority to U.S. provisional application 62/211,597 filed on Aug. 28, 2015 and is a continuation-in part of PCT application PCT/US15/28062, filed on Apr. 28, 2015 which claims priority to U.S. provisional application Nos. 61/985,983 filed on Apr. 29, 2014 and 61/987,433 filed on May 1, 2014. Each of these earlier filed applications are hereby incorporated by reference in its entirety.

GOVERNMENT SUPPORT

This invention was made with government support under National Institutes of Health (NIH) grant number MH098977 awarded by the Public Health Service (PHS). The government has certain rights in the invention.

BACKGROUND

The determination of the mRNA content of a cell or tissue (i.e. "gene expression profiling") provides a method for the functional analysis of normal and diseased tissues and organs. Gene expression profiling is usually performed by isolating mRNA from tissue samples and subjecting this mRNA to microarray hybridization. However, such methods only allow previously known genes to be analyzed, and cannot be used to analyze alternative splicing, promoters and polyadenylation signals. Additionally, microarrays have two major shortcomings: they are linked to known genes, and they have limited sensitivity and dynamic range.

Direct sequencing of all, or parts, of the mRNA content of a tissue is being increasingly used. However, current methods of analyzing the mRNA content of cells by direct sequencing rely on analyzing bulk mRNA obtained from tissue samples typically containing millions of cells. This means that much of the functional information present in single cells is lost or blurred when gene expression is analyzed in bulk mRNA. In addition, dynamic processes, such as the cell cycle, cannot be observed in population averages. Similarly, distinct cell types in a complex tissue (e.g. the brain) can only be studied if cells are analyzed individually.

There are often no suitable cell-surface markers to use in isolating single cells for study, and even when there are, a small number of single cells are not sufficient to capture the range of natural variation in gene expression. What is needed is a method of preparing cDNA libraries which can be used to analyze gene expression in a plurality of single cells.

SEQUENCE LISTING

The present application is being filed along with a Sequence Listing in electronic format. The Sequence Listing is provided as an ASCII file entitled IP-1388-US SL.txt, created Oct. 12, 2015, which is 6,742 bytes in size. The information in the electronic format of the Sequence Listing is incorporated herein by reference in its entirety.

SUMMARY

Presented herein are methods and compositions for nucleic acid analysis from single cells and/or nucleic acid from single cell nuclei and organelles. Some methods and compositions can be used for multiplexed single cell gene expression analysis. Some methods and compositions include the use of droplets and/or beads bearing unique barcodes such as unique molecular barcodes (UMI).

In one embodiment, presented herein are methods and compositions of nucleic acid sequence analysis from a single cell. In some embodiments, the methods and compositions of nucleic acid sequence analysis can be used to prepare sequencing library from nucleic acid from a single organelle. In some embodiments, the organelle can be a nuclei from a single cell. In some embodiments, the single organelle is obtained from single cell. Other exemplary organelles include but are not limited to mitochondria and ribosome.

In one embodiment, the methods include releasing nuclei from cells to provide plurality of nuclei, wherein each nucleus is from a single cell. The nuclei are spatially separated from each other such that one nucleus is present at a spatial compartment. A first strand of cDNA is synthesized from the mRNA in each individual mRNA sample with a first strand synthesis primer. In some embodiments, the first strand synthesis primer is an oligo dT primer further comprising a first amplification primer binding site. In some embodiments, the first strand synthesis primer is a randomer. In some embodiments, the first strand synthesis primer is a randomer further comprising a first amplification primer binding site. In some embodiments, the first strand synthesis primer is a mixture of oligo dT primer and randomer each further comprising a first amplification primer binding site. In some embodiments, the method further includes incorporating a template switching oligonucleotide primer (TSO primer) along with the mixture of oligo dT primer and randomer, each of oligo dT primer and randomer further comprising a first amplification primer binding site. In some embodiments, the TSO primer further comprises a second amplification primer binding site. In some embodiments, the first strand synthesis primer is extended beyond the mRNA template and further copies the TSO primer strand. In some embodiments, the second strand of cDNA is synthesized using the TSO primer. In some embodiments, the second strand of cDNA is synthesized using the second amplification primer complimentary to the first strand of cDNA that is extended beyond the mRNA template to encompass the complimentary TSO strand. In some embodiments, the double stranded cDNA is amplified with first and second amplification primers. In some embodiments, the first, second or both first and second amplification primers are immobilized on a solid support. Exemplary solid supports include beads, flow cells, microwells In some embodiments, the double stranded cDNA is subjected to tagmentation reaction such that barcodes can be introduced into the double stranded cDNA. Exemplary methods of tagmentation are disclosed in U.S. Pat. Nos. 9,115,396; 9,080,211; 9,040,256; U.S. patent application publication 2014/0194324. Each of which is incorporated herein by reference in its entirety. In some embodiments, the barcodes can be used to determine the contiguity information of the sequence. In some embodiments, the barcodes can be used as a source identifier.

In some embodiments, the method includes incorporating a tag into the cDNA to provide a plurality of tagged cDNA samples, wherein the cDNA in each tagged cDNA sample is complementary to mRNA from a single cell. In one embodiment, the tag comprises a cell-specific identifier sequence and a unique molecular identifier (UMI) sequence. In some embodiments, the first strand synthesis primer comprises a tag. In some embodiments, the TSO primer comprises a tag.

In some embodiments, tagged cDNA from the nuclei of single cells can be pooled and optionally amplified.

In some embodiments, the methods include preparing sequencing library from microRNA (miRNA), small interfering RNA (siRNA), ribosomal RNA, or mitochondrial DNA from a single cell. The method includes releasing the cell organelles from a single cell to provide plurality of organelles. The organelles are spatially separated from each other such that one organelle is present at a spatial compartment. A first strand of DNA is synthesized from the microRNA (miRNA), small interfering RNA (siRNA), ribosomal RNA, or mitochondrial DNA with a first strand synthesis primer. In some embodiments, the first strand synthesis primer is a randomer. In some embodiments, the first strand synthesis primer is a randomer further comprising a primer binding site. In some embodiments, the first strand synthesis primer is a mixture of a first strand specific synthesis primer and a randomer. In some embodiments, the first strand synthesis primer is a mixture of a first strand specific synthesis primer and a randomer, each further comprising a first amplification primer binding site.

In some embodiments, the primer that binds to the first primer binding site is an amplification primer. In some embodiments, the method further includes incorporating a template switching oligonucleotide primer (TSO primer) along with the mixture of a first strand specific synthesis primer and a randomer, each of first strand specific synthesis primer and a randomer further comprising a first primer binding site. In some embodiments, the TSO primer further comprises a second primer binding site. In some embodiments, the primer that binds to the second primer binding site is an amplification primer. In some embodiments, the first strand synthesis primer is extended beyond the microRNA (miRNA), small interfering RNA (siRNA), ribosomal RNA, or mitochondrial DNA template and further copies the TSO primer strand. In some embodiments, the second strand of DNA is synthesized using the TSO primer. In some embodiments, the second strand of DNA is synthesized using the second primer complimentary to the first strand of DNA that is extended beyond the template RNA or DNA to encompass the complimentary TSO strand. In some embodiments, the double stranded DNA is amplified with first and second primers.

In one embodiment, the organelles such as nuclei, mitochondria, ribosomes are spatially separated by fluorescence activated cell sorting (FACS) and each organelle is sorted into a spatial compartment, e.g., single microwell on a Fluidigm C1 chip. In some embodiments, each organelle is spatially separated into a spatial compartment by being immobilized on a solid surface. For example, through an antibody, wherein the antibody specifically binds to the organelle and the antibody is immobilized on a solid surface. In some embodiments, the solid surface is a flow cell or a bead.

In some embodiments, the randomers comprise one or more quasi-random primers that are selected from the group consisting of an AT-rich set of random amplification primers; a set of random amplification primers comprising AT-rich 5' termini; a set of variable-length random amplification primers, wherein each primer comprises a random 3' portion and a degenerate 5' terminus, the degenerate 5' terminus of which can be proportional in length to the A/T content of the random 3' portion of the primer; a set of Tm-normalized random primers, wherein each primer of the set comprises one or more base analogues that can normalize the Tm of each primer to the Tm of other primers in the set of primers; a set of random primers, wherein each primer comprises a random 3' portion and a constant 5' priming portion; a set of random amplification primers, wherein each primer comprises a random 3' portion and a constant 5' priming portion, and wherein the random 3' portion comprises RNA; a set of random amplification primers, wherein each primer comprises a random 3' portion and a constant 5' priming portion, and wherein the random 3' portion comprises at least one non-natural base selected from the group consisting of nucleic acids including 2'-deoxy-2-thiothymidine (2-thio-dT), 2-aminopurine-2'-deoxyriboside (2-amino-dA), N4-ethyl-2'-deoxycytidine (N4-Et-dC), N4-methyl deoxycytidine (N4-Me-dC), 2'-deoxyinosine, 7-deazaguanine (7-deaza-G), 7-iodo-7-deazaguanine (I-deazaG), 7-methyl-7-deazaguanine, (MecG), 7-ethyl-7-deazaguanine (EtcG) and any combination of the foregoing sets of primers. The quasi-random primers set forth above are described in further detail herein. In some embodiments described herein, the quasi-random primers are provided in pairs or sets.

One embodiment presented herein is a method of preparing a cDNA library from a plurality of single cells, the method comprising the steps of: releasing mRNA from each single cell to provide a plurality of individual mRNA samples, wherein the mRNA in each individual mRNA sample is from a single cell; synthesizing a first strand of cDNA from the mRNA in each individual mRNA sample with a first strand synthesis primer and incorporating a tag into the cDNA to provide a plurality of tagged cDNA samples, wherein the cDNA in each tagged cDNA sample is complementary to mRNA from a single cell. In one embodiment, the tag comprises a cell-specific identifier sequence and a unique molecular identifier (UMI) sequence. In some embodiments, the tag comprises a cell-specific identifier sequence without the UMI. The method further comprises pooling the tagged cDNA samples; optionally amplifying the pooled cDNA samples to generate a cDNA library comprising double-stranded cDNA; and performing a tagmentation reaction to simultaneously cleave each cDNA and incorporate an adapter into each strand of the cDNA, thereby generating a plurality of tagged cDNA fragments. In some embodiments, sufficient number of single cells is present, the amplification of cDNA can be avoided. The second strand of cDNA is synthesized using a template switching oligonucleotide primer (TSO primer), followed by symmetric Nextera.

In certain embodiments, the method further comprises amplifying the tagged cDNA fragments to generate amplified tagged cDNA fragments. In some aspects, amplifying comprises adding additional sequence to the 5' end of the amplification products.

In some aspects, the additional sequence comprises primer binding sequence for amplification on a solid support. In some aspects, the additional sequence comprises additional index sequences.

In certain embodiments, the method further comprises amplifying the amplified tagged cDNA fragments on a solid support.

In certain embodiments, the method further comprises sequencing the amplification products on the solid support.

In some aspects, the tagmentation reaction comprises contacting the double-stranded cDNA with a transposase mixture comprising adapter sequences that are not found in the first strand synthesis primer.

In some aspects, the transposase mixture consists essentially of transposomes having one type of adapter sequence.

In certain embodiments, the method further comprises sequencing the tagged cDNA fragments.

In some aspects, sequencing comprises 3' tag counting.

In some aspects, sequencing comprises whole transcriptome analysis.

In some aspects, first strand synthesis is performed using a mixture of random primers, the random primers further comprising a tag.

In some aspects, the first strand synthesis primer comprises a double-stranded portion. In some embodiments, the first strand synthesis primer comprising a double-stranded portion further comprises a single stranded loop at one end. In some aspects, the first strand synthesis primer comprises a region capable of forming a hairpin.

In some aspects, the first strand synthesis primer reduces concatenation byproducts compared to a single-stranded first strand synthesis primer.

In some aspects, the first strand synthesis primer comprises a region of RNA.

In some aspects, the first strand synthesis primer is hybridized to a complementary oligonucleotide, thereby forming a double stranded portion.

Also presented herein is a plurality of beads, wherein each bead comprises a plurality of oligonucleotides, each oligonucleotide comprising: (a) a linker; (b) an amplification primer binding site; (c) optionally a Unique Molecular Identifier which differs for each oligonucleotide; (d) a bead-specific sequence that is the same on each oligonucleotide on the bead but is different on other beads; and (e) a capture sequence for capturing mRNAs and priming reverse transcription.

In some aspects, the capture sequence comprises oligodT.

In some aspects, each bead is in a separate droplet segregated from other beads.

The details of one or more embodiments are set forth in the accompanying drawings and the description below. Other features, objects, and advantages will be apparent from the description and drawings, and from the claims.

BRIEF DESCRIPTION OF THE DRAWINGS

FIG. 6 is a table comparing methods of gene expression analysis using 100 pg human brain reference RNA.

FIG. 7 is a table comparing methods of high throughput single cell gene expression analysis using single cells.

FIG. 14 shows the steps of cDNA synthesis from single nuclei.

FIG. 15 is a schematic showing cDNA synthesis using the template switch SMARTer method. Figure discloses SEQ ID NOS 14, 14, 22, 14, and 22, respectively, in order of appearance.

FIG. 17 shows the advantages if the SMART-Plus assay method. FIG. 17A shows the assay performance of SMART-plus assay compiled from more than 1000 high quality single nuclei. FIG. 17B shows the transcript coverage data.

DETAILED DESCRIPTION

Presented herein are methods and compositions for multiplexed single cell gene expression analysis. Some methods and compositions include the use of droplets and/or beads bearing unique barcodes such as unique molecular barcodes (UMI).

Figure 1:
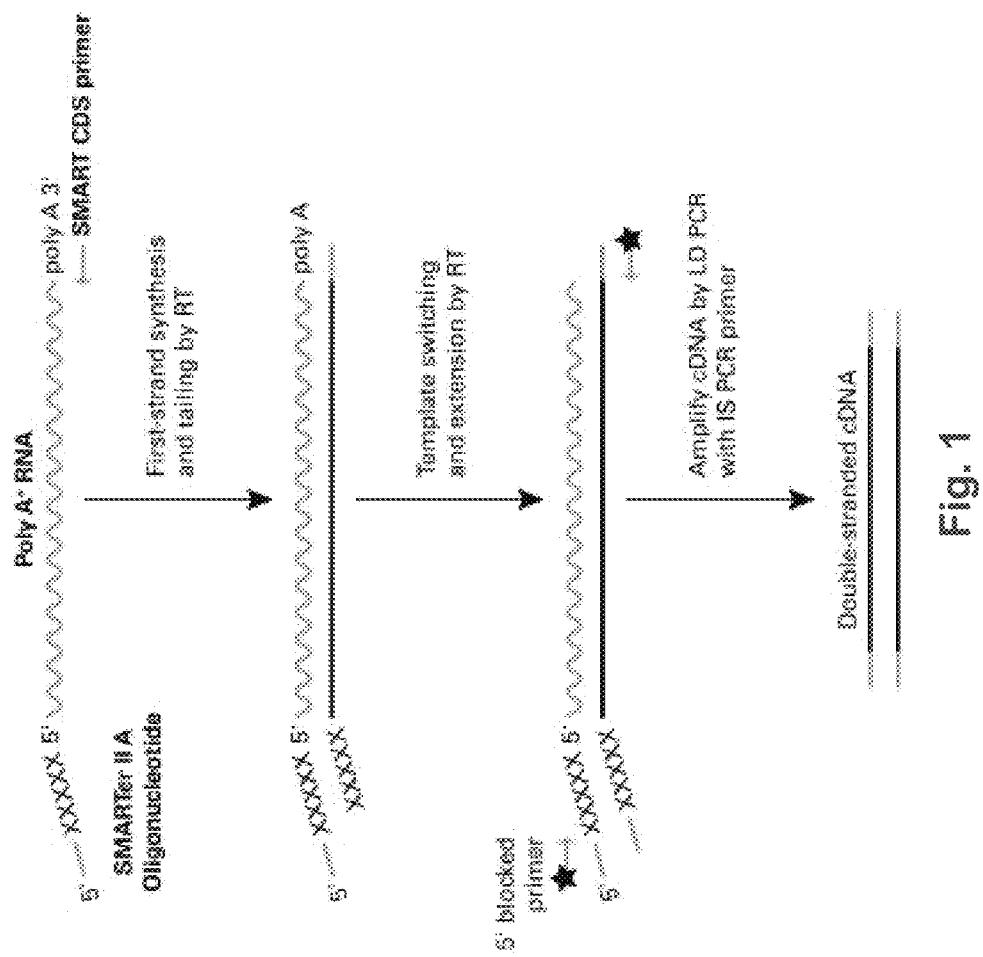
FIG. 1 is an exemplary schematic showing a schematic of cDNA synthesis using SMARTer methodology.

Currently the most commonly used method for single cell RNA-Seq is based on CLONTECH™ SMART-SEQ™ technology or derivatives thereof. In short, an oligo(dT) primer primes the first-strand cDNA synthesis reaction. When the reverse transcriptase (SMARTSCRIBE™) reaches the 5' end of the mRNA, the enzyme's terminal transferase activity adds a few additional non-template nucleotides to the 3' end of the cDNA. A template-switch oligo, designed to base-pair with this non-template nucleotide stretch, anneals and creates an extended template to enable the RT continue replicating to the end of the oligonucleotide (FIG. 1).

The methods presented herein can include methods of generating tagged cDNA with sample-specific tags as described, for example, in the disclosure of U.S. 2012/0010091, the content of which is incorporated herein by reference in its entirety. As used herein, the terms single-cell tagged reverse transcription and STRT refer to methods disclosed, for example in the incorporated materials of U.S. 2012/0010091. In some embodiments, the double stranded cDNA is not degraded with DNase in the STRT method. Instead, the double stranded cDNA is tagmented with a transposase, for example, standard Nextera.

The double stranded cDNA can then be converted into a sequencing library using for example NEXTERA™ or TRUSEQ™ (Illumina, Inc.) for whole transcriptome RNA-Seq; or through enzymatic degradation, such as DNase I or Fragmentase, followed by adaptor ligation for 5' end sequencing. Both methods have pros and cons: the former can only be multiplexed after sample barcodes have been introduced during the library prep whereas the latter can be multiplexed after cDNA synthesis as barcodes can be introduced during the 1st strand synthesis step. Therefore higher throughput and lower cost per sample favor the latter. However, the information obtained with both methods has different applications: the former allows for sequencing of the whole transcriptome whereas the latter interrogates gene expression levels only.

Herein are presented rapid gene expression library preparation methods that can be applied to single cell input levels and that allows for high levels of sample multiplexing early on in the protocol.

Figure 2A:
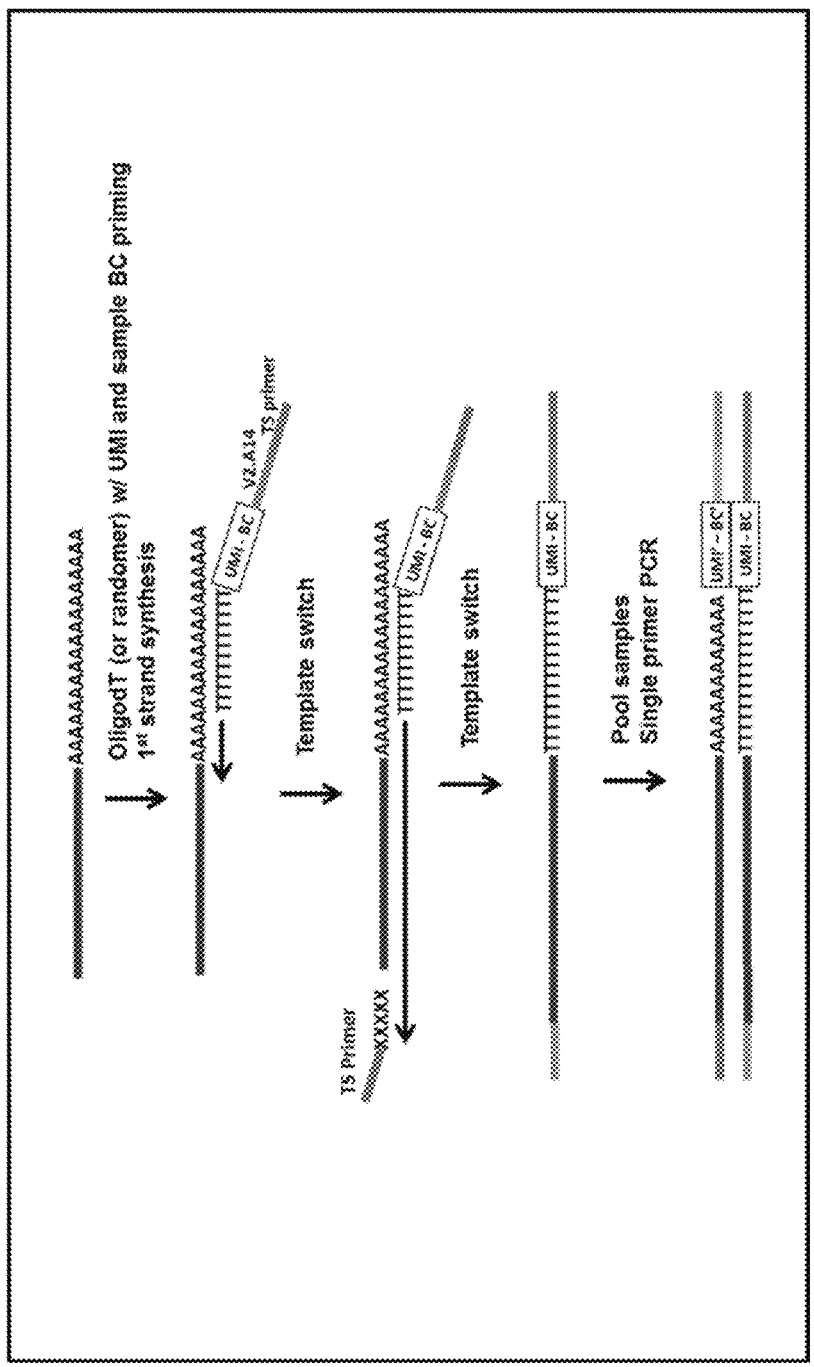
FIG. 2A is an exemplary schematic showing first strand synthesis according to one embodiment, primed with oligo dT that has been appended with an optional molecular barcode (UMI), a sample barcode (BC), an amplification primer binding sequence (V2.A14) and a template switch (TS) primer sequence, followed by template switching, pooling of samples and single primer PCR. Figure discloses SEQ ID NOS 14, 14-15, 14-17, and 16, respectively, in order of appearance.

In some embodiments, first strand synthesis is primed with an (anchored) oligo dT primer (or potentially with a randomer or a combination of the two) that is appended with a sample barcode (BC), an amplification primer binding site, and optionally a template switch (TS) primer sequence. In some embodiments, the amplification primer binding site is a transposase adapter sequence, such as, for example, the Nextera adaptor sequence V2.A14 or V2.B15. The barcode can be preceded or followed by a molecular barcode (unique molecular identifier, or "UMI") that would allow for the detection of PCR duplicates. When the reverse transcriptase reaches the 5' end of the mRNA, template switch occurs as described above and in the incorporated materials of U.S. 2012/0010091. This incorporates the complement of the TS primer sequence into the 1st strand cDNA. Because a sample barcode has been introduced into the 1st strand cDNA, different samples can at this point be pooled. The 1st strand pool will subsequently be rendered double stranded and optionally amplified in a PCR reaction with the TS primer (FIG. 2A). Due to the fact that both ends of the cDNA contain complementary sequences, formation of hairpin structures will result in suppression of amplification of smaller fragments such as artifacts, etc.

Figure 3A:
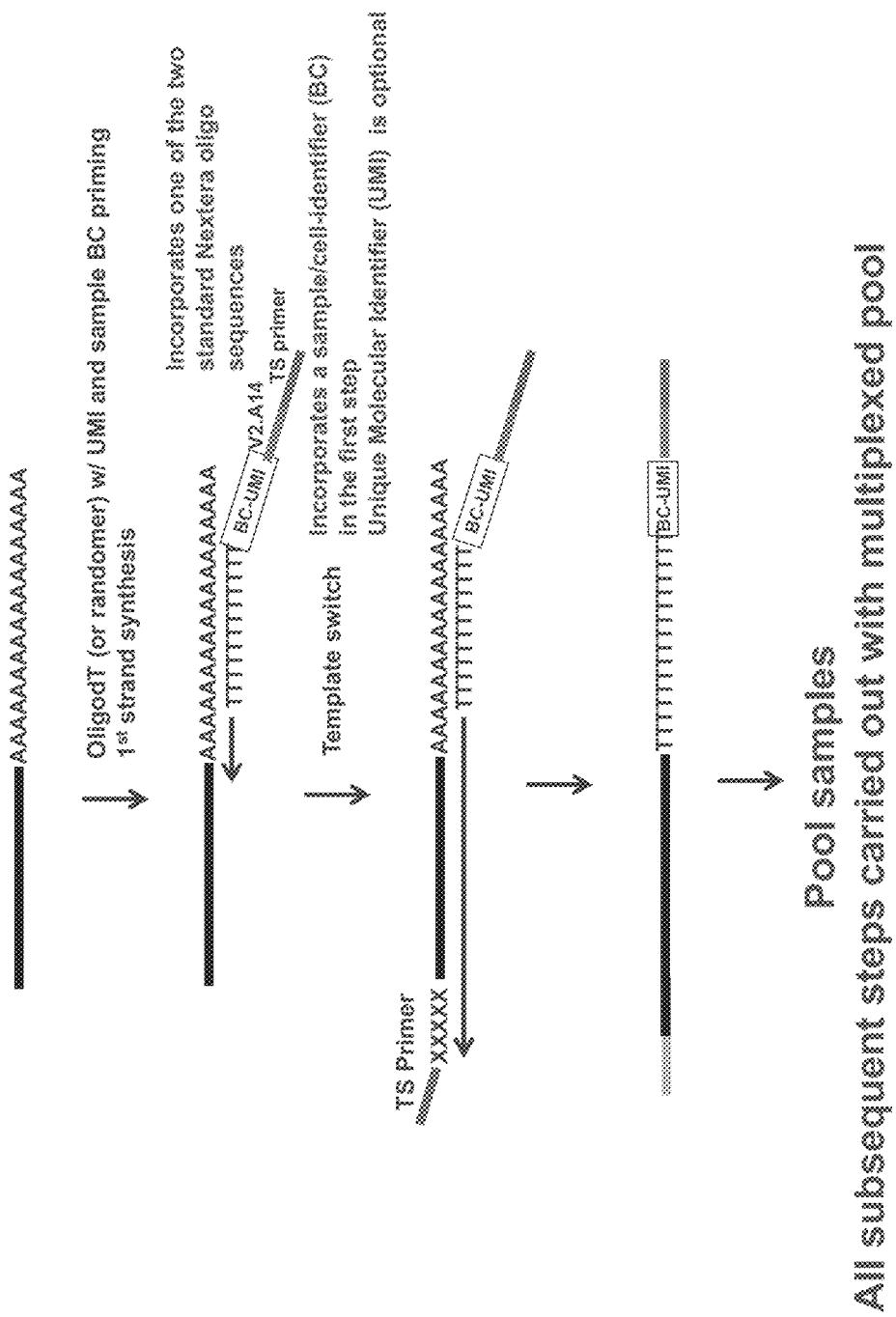
FIG. 3A is an exemplary schematic first strand synthesis according to one embodiment, primed with oligo dT that has been appended with a sample barcode (BC), an optional molecular barcode (UMI), an amplification primer binding sequence (V2.A14) and a template switch (TS) primer sequence, followed by template switching, pooling of samples and single primer PCR. The optional UMI is at the 5'-end of the BC. Figure discloses SEQ ID NOS 14, 14-15, and 14-16, respectively, in order of appearance.

In some embodiments, as set forth in FIGS. 2A and 3A, 1st strand synthesis is primed with an oligo dT that has been appended with a sample barcode (BC), a copy of a transposase adaptor sequence (the "Nextera V2.A14 sequence"), optionally with a molecular barcode (UMI), and the template switch (TS) primer sequence. Template switch at the 3' end of the cDNA strand incorporates TS' primer sequence at the other end of the 1st strand. cDNAs of different samples can be pooled at this point.

Figure 2B:
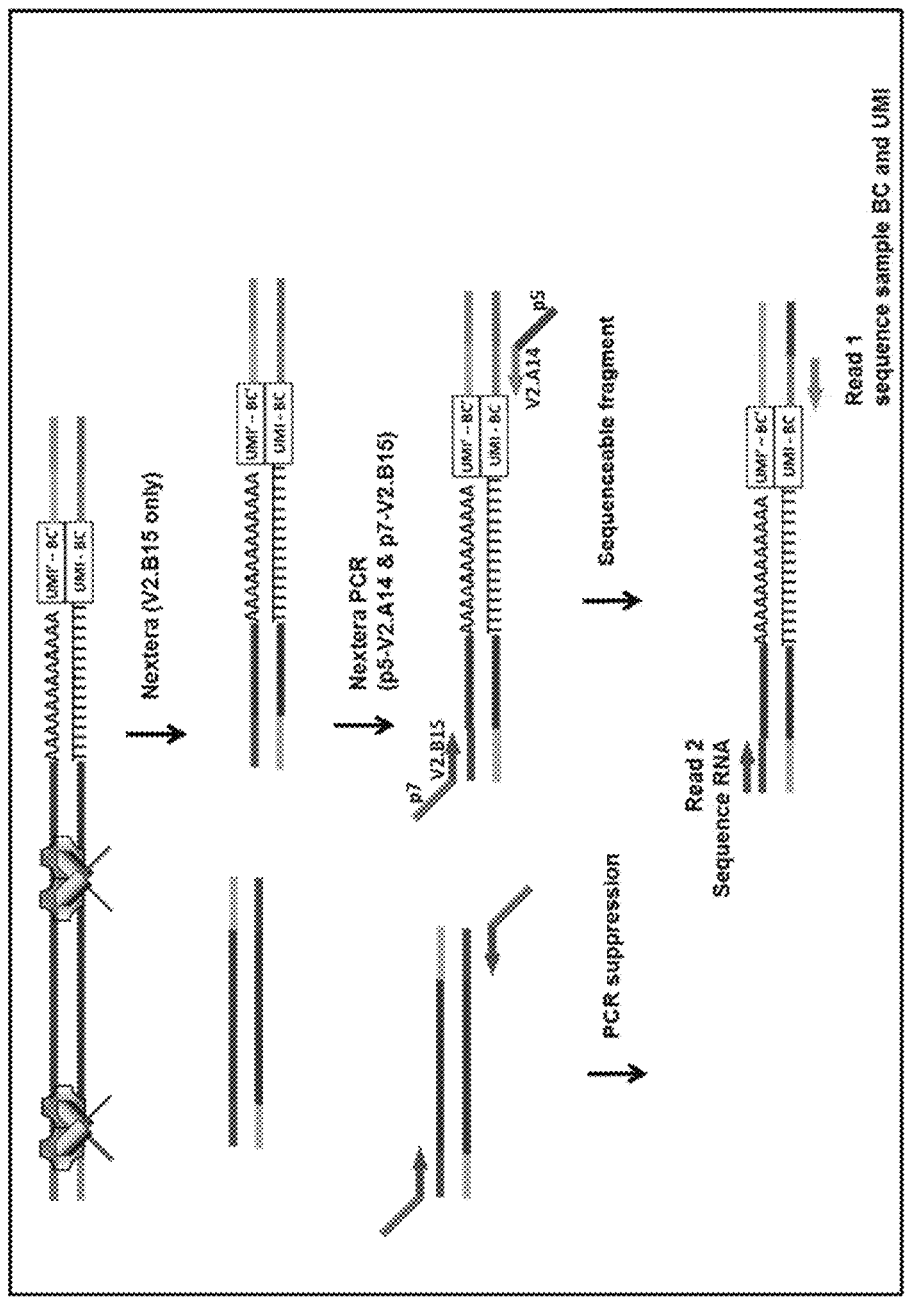
FIG. 2B is an exemplary schematic showing tagmentation of pooled amplification products with symmetric Nextera, followed by amplification using different forward (V2.615) and reverse (V2.A14) PCR primers and subsequent paired end sequencing. Figure discloses SEQ ID NOS 17, 16, 17, 16, 17, 16, 17, and 16, respectively, in order of appearance.
Figure 3B:
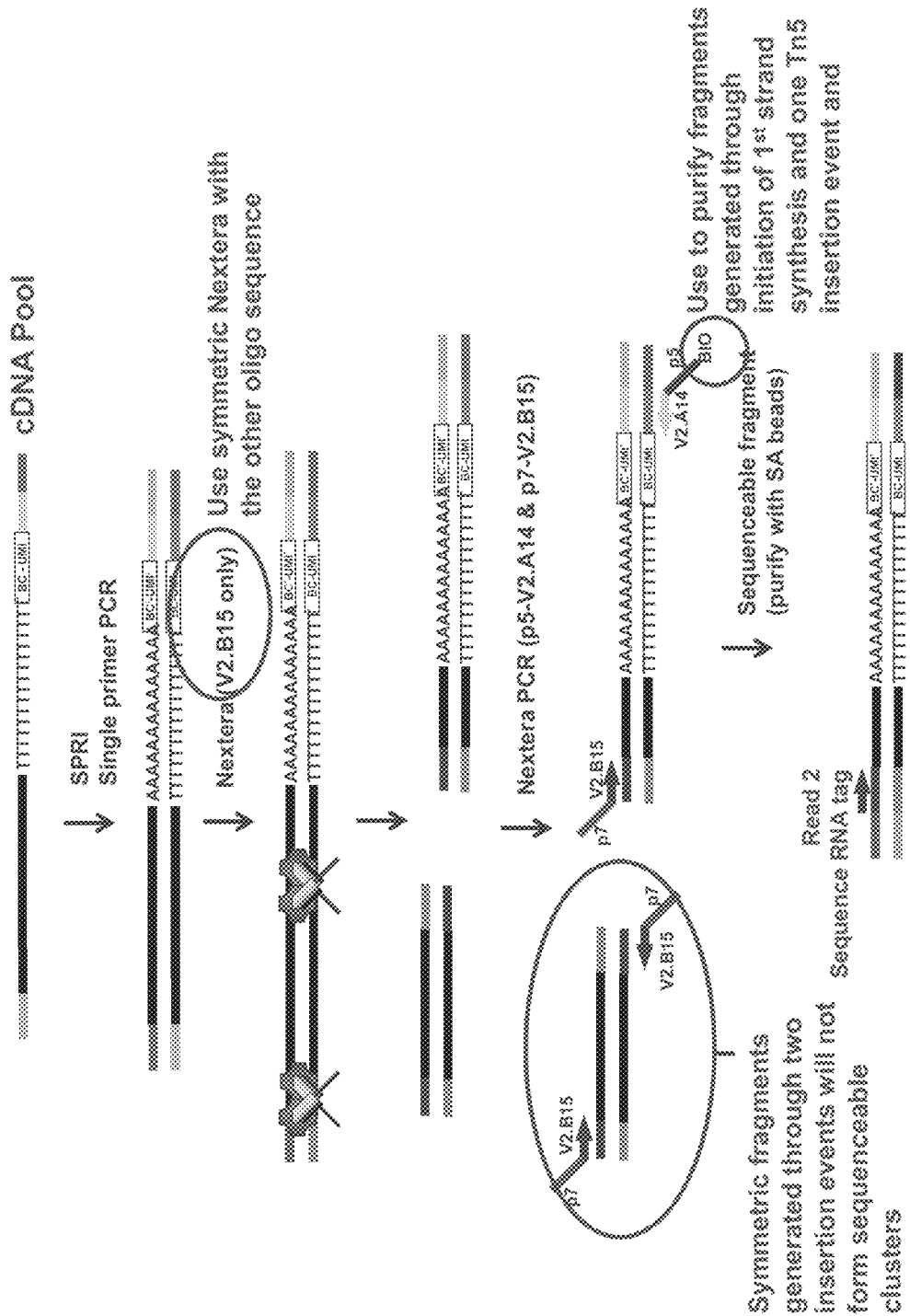
FIG. 3B is an exemplary schematic showing tagmentation of pooled amplification products, amplification and sequencing according to one embodiment. Figure discloses SEQ ID NOS 16, 18, 16, 18, 16, 18, 16, 18, 16, 18, and 16, respectively, in order of appearance.

In some embodiments, as set forth in FIGS. 2B and 3B, the cDNAs are amplified with a TS oligo. This single primer PCR will suppress small amplicons such as primer dimer, etc. The cDNA pool can be tagmented with a transposase, for example, ("NEXTERA™") that only contains one adaptor sequence, rather than the typical two adapters. In the example shown in FIGS. 2B and 3B, transposases are loaded with V2.B15 oligos. After tagmentation, PCR with p5-V2.A14 and p7-V2.B15 amplification primers preferentially amplifies the 3' end fragments of the cDNA. Fragments that were generated by two tagmentation events ("symmetric fragments") will be suppressed during the PCR and will not generate sequenceable fragments. For example, as shown in FIGS. 2B and 3B, amplification products generated from symmetric fragments will present P7 primer sequence at both the 5' and 3' end of the amplification product, and will not form sequenceable clusters on a standard Illumina flowcell bearing P5 and p7 amplification primers. Additionally, they will be suppressed during PCR due to their complementary ends. In contrast, the 3' terminal fragment will bear P5 and P7 primer binding sites after amplification, and can form sequenceable clusters on an Illumina flowcell. Paired end sequencing will result in the sample BC and UMI sequence during read 1 and cDNA sequence during read 2.

Accordingly, in certain embodiments presented herein, rather than performing sequencing of the entire transcript, a form of a digital gene expression assay is performed that relies on 3' tag counting. The methods presented herein offer the ability to individually barcode cells at the first strand synthesis step. Additionally, barcoding of the 3' end of cDNA with inexpensive oligo-dT primers or randomers provides significant cost savings advantages. Furthermore, use of randomers for cDNA synthesis is advantageous because it makes the method more similar to total-RNA seq protocol in addition to 3'-tag counting assay.

Figure 5:
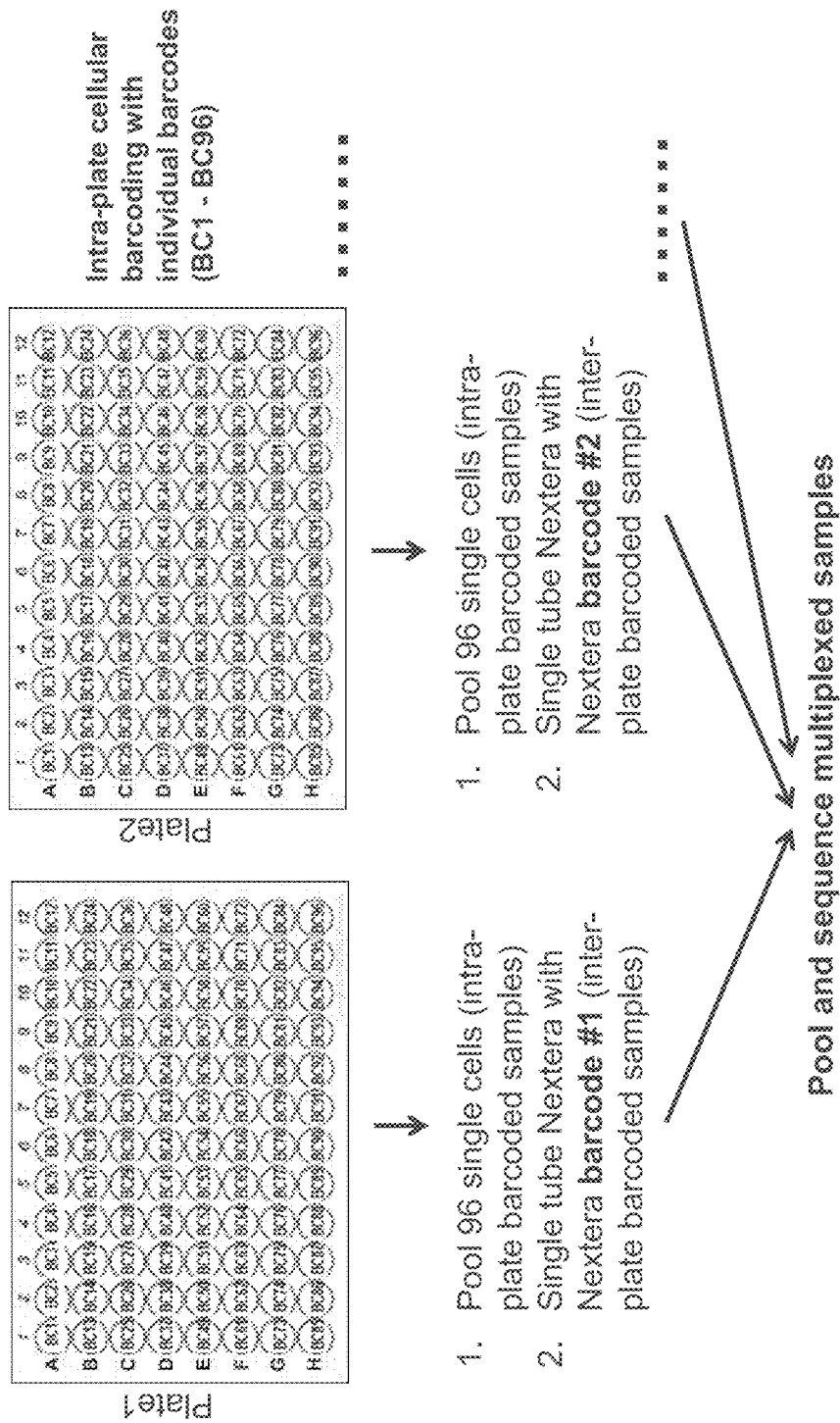
FIG. 5 is an exemplary schematic showing a method of pooling and sequencing multiplexed samples according to one embodiment.

Subsequent pooling, cleanup, single primer cDNA PCR amplification, tagmentation and sequencing library prep can be performed in a single tube for 2, 3, 4, 5, 6, 7, 8, 9, 10, 20, 30, 40, 50, 60, 70, 80, 90, 91, 92, 93, 94, 95, 96, 97, 98, 99, 100 or more than cells. Thus, the methods and compositions described herein are highly amenable to multiplexing. As an example, set forth in FIG. 5, the methods provided herein enable multiplexing at cellular levels (e.g., 96 samples per 96-well plate), Further, the methods enable further multiplexing at the plate level using uniquely barcoded plates (e.g., tagmentation to incorporate a barcode that identifies the 96 well plate). These methods are amenable to automation and can provide signification cost and time savings.

It will be appreciated that the order of a sample barcode and UMI on the first strand synthesis primer can be varied. For example, in some embodiments, the sample barcode (BC) is positioned 3' to the UMI. In some embodiments, the sample barcode (BC) is positioned 5' to the UMI. In some embodiments, the sample barcode (BC) is directly contiguous with the UMI. In some embodiments, the sample barcode (BC) is separated from the UMI by 1, 2, 3, 4, 5, 6, 7, 8, 9, 10 or more than 10 nucleotides. In some embodiments, the sample barcode (BC) overlaps with the UMI by 1, 2, 3, 4, 5, 6, 7, 8, 9, 10 or more than 10 nucleotides.

Figure 4A:
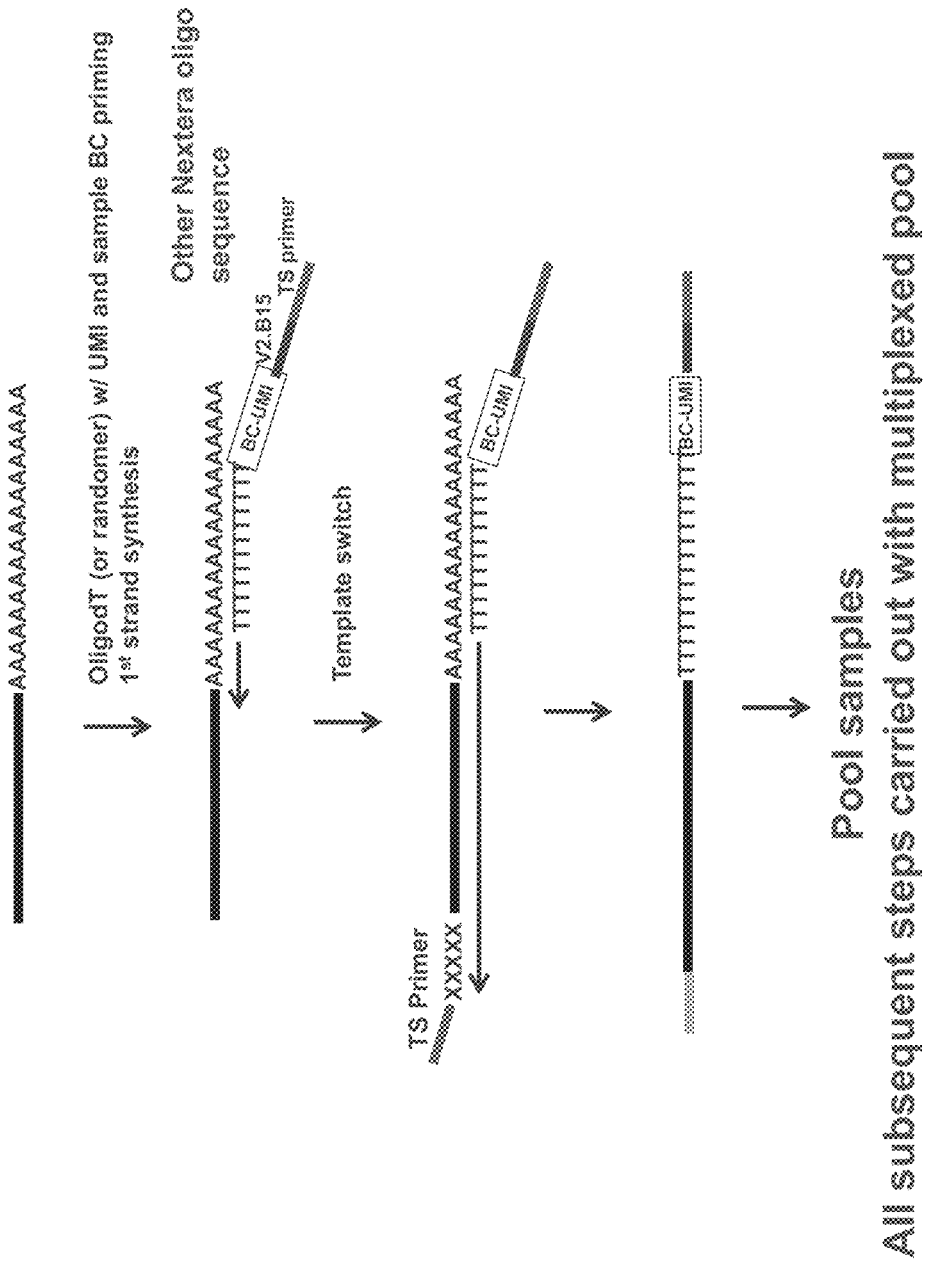
FIG. 4A is an exemplary schematic showing first strand synthesis according to one embodiment. Figure discloses SEQ ID NOS 14 14-15, and 14-16, respectively, in order of appearance.
Figure 4B:
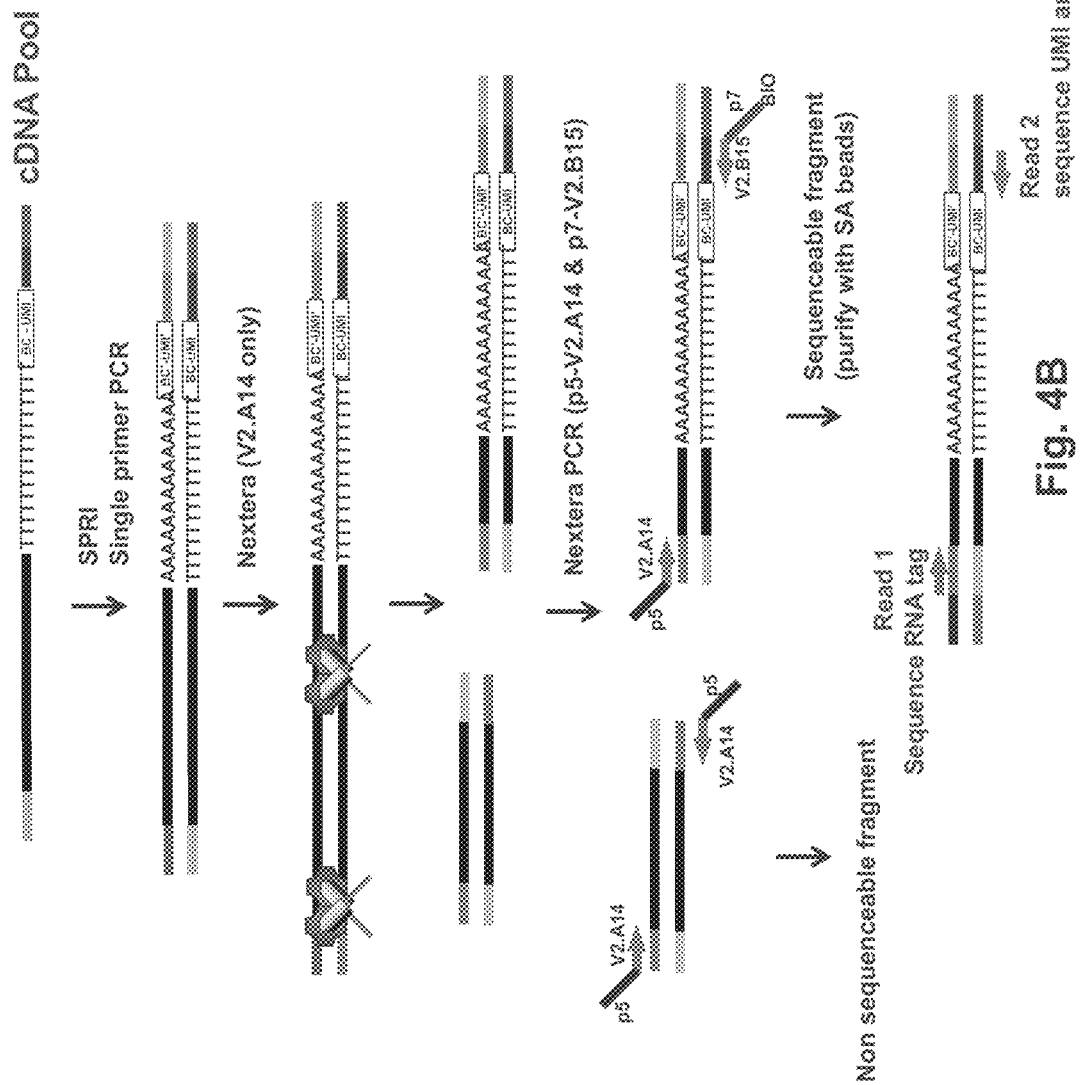
FIG. 4B is an exemplary schematic showing tagmentation of pooled amplification products, amplification and sequencing according to one embodiment. Figure discloses SEQ ID NOS 16, 18, 16, 18, 16, 18, 16, 18, 16, 18, and 16, respectively, in order of appearance.

In some embodiments, tagmentation is performed using a transposase mixture that contains adapter sequences that are not found in the first strand synthesis primer. Doing so produces tagmentation fragments that bear different adapter sequences compared to the sequence incorporated into the first strand synthesis primer. For example, in some embodiments, the transposase mixture exclusively comprises transposomes having one type of adapter sequence. Fragments that were generated by this type of mixture are referred to herein as "symmetric fragments" and do not produce sequenceable clusters on an Illumina flowcell. In some embodiments, the transposase mixture may comprise some amount of the sequence incorporated into the first strand synthesis primer, wherein the amount is low enough to still allow all or substantially all of the 3' cDNA fragments to be amplified and sequenced. For example, the adapter sequences in the transposome mixture may comprise less than 0.01%, 0.1%, 1%, 2%, 3%, 4%, 5%, 6%, 7%, 8%, 9%, 10%, 11%, 12%, 13%, 14%, 15%, 16%, 17% 18%, 19%, 20%, or less than 25%, 30%, 35%, 40%, 45% or less than 50% of the sequence incorporated into the first strand synthesis primer. It will be appreciated that where two transposase adapters are typically used, either one of the two adapters can be incorporated into the first strand synthesis primer, and the other adapter can be used during the tagmentation event. For example, in the exemplary embodiments set forth in FIGS. 3A, 3B, 4A and 4B, where one adapter sequence is incorporated into the first strand synthesis primer, that adapter is not used in the tagmentation mixture. FIGS. 3A and 3B show one embodiment where adaptor V2.A14 is incorporated into the first strand synthesis primer and adapter V2.B15 is used as the transposome adapter during the tagmentation step. FIGS. 4A and 4B show an alternative embodiment where adaptor V2.B15 is incorporated into the first strand synthesis primer and adapter V2.A14 is used as the transposome adapter during the tagmentation step. In both instances, the resulting tagmentation fragments fall in to two categories: symmetric fragments (unable to be amplified and/or sequenced), and asymmetric fragments which can be amplified using a set of V2.A14 and V2.B15 primers.

In some embodiments, the number of single cells that can be multiplexed is significantly increased by incorporating indexes into the transposome adapter sequences. As exemplified in FIG. 5, each individual cell can be identified using a cell-specific barcode and each set of cells (for example, a plate of 96 cells) can be contacted with a tagmentation mixture having a plate-specific barcode incorporated into the transposome adapter sequence. In the example shown in FIG. 5, the cDNAs from each of the 96 cells on a plate are pooled prior to tagmentation, and then the tagmented samples are pooled for multiplexed sequencing. It will be appreciated that any number of cells can be pooled prior to tagmentation, and that use of a 96 well plate is simply one of a variety of embodiments. For example, a set of 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, or more than 100, 200, 300, 400, 500, 600, 700, 800, 900 or more than 1000, and any intermediate number of cells may be pooled for tagmentation. First strand synthesis may take place in any single or multi-well vessel, such as a multi-well plate, chip, microfluidic device, emulsion, bead mixture, or any other suitable format for multiplex handling of a plurality of cells.

Figure 8:
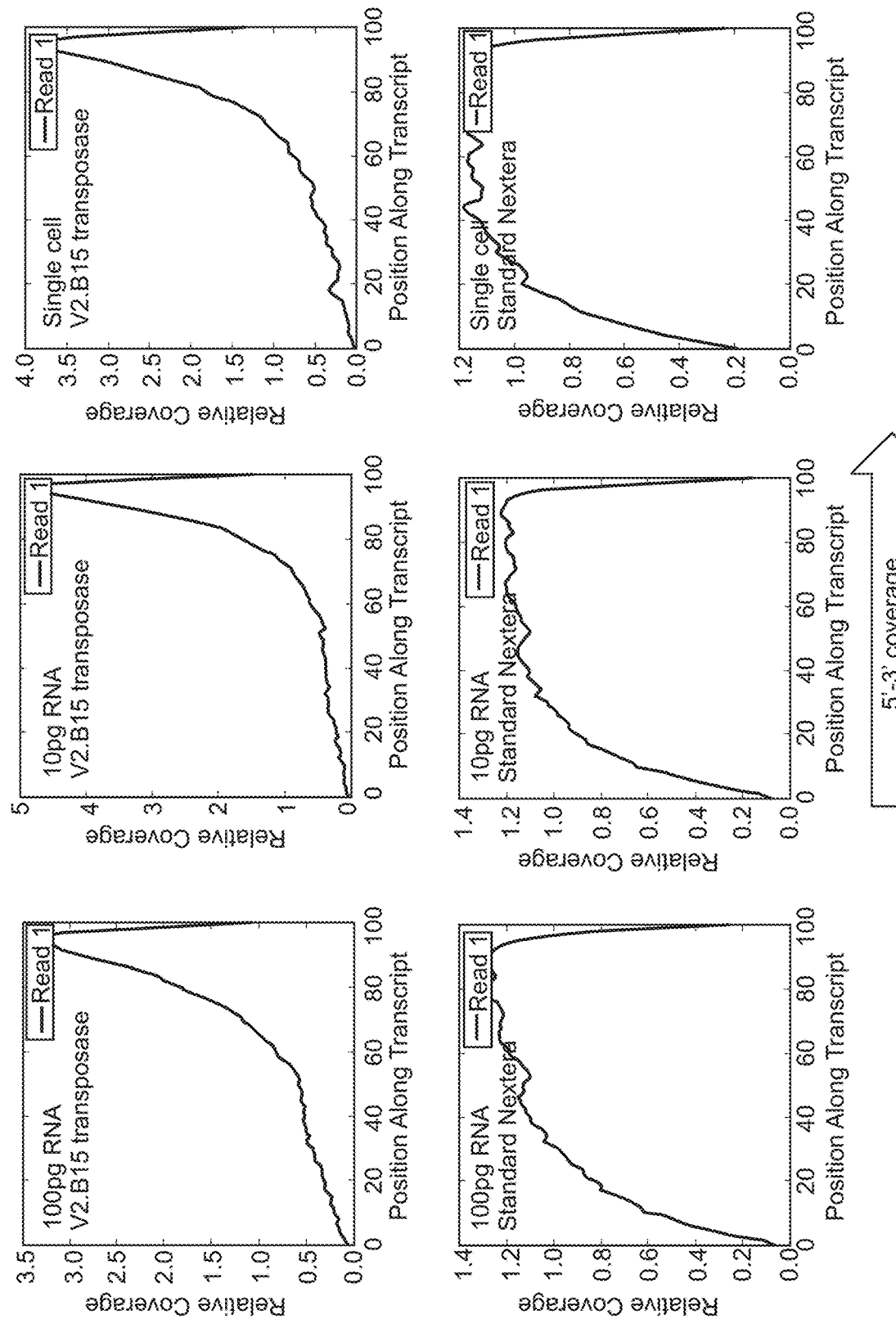
FIG. 8 shows graphs comparing transcript coverage with tagmentation using only one transposase adaptor (V2.B15) versus tagmentation using standard/asymmetric tagmentation, using two transposase adaptors (V2.A14 and V2.B15).

As shown in FIG. 7 (single cells), when gene expression was analyzed using either symmetric tagmentation (Nextera version V2.B15) compared to asymmetric tagmentation (Nextera version V2.B15/V2.A14) a significant number of genes were detected and other metrics were obtained. FIG. 8 shows that transcript coverage is almost entirely biased towards the 3' end of the transcripts when performing tagmentation using only one transposase adaptor (V2.B15) versus tagmentation using two transposase adaptors (V2.A14 and V2.B15).

Figure 11:
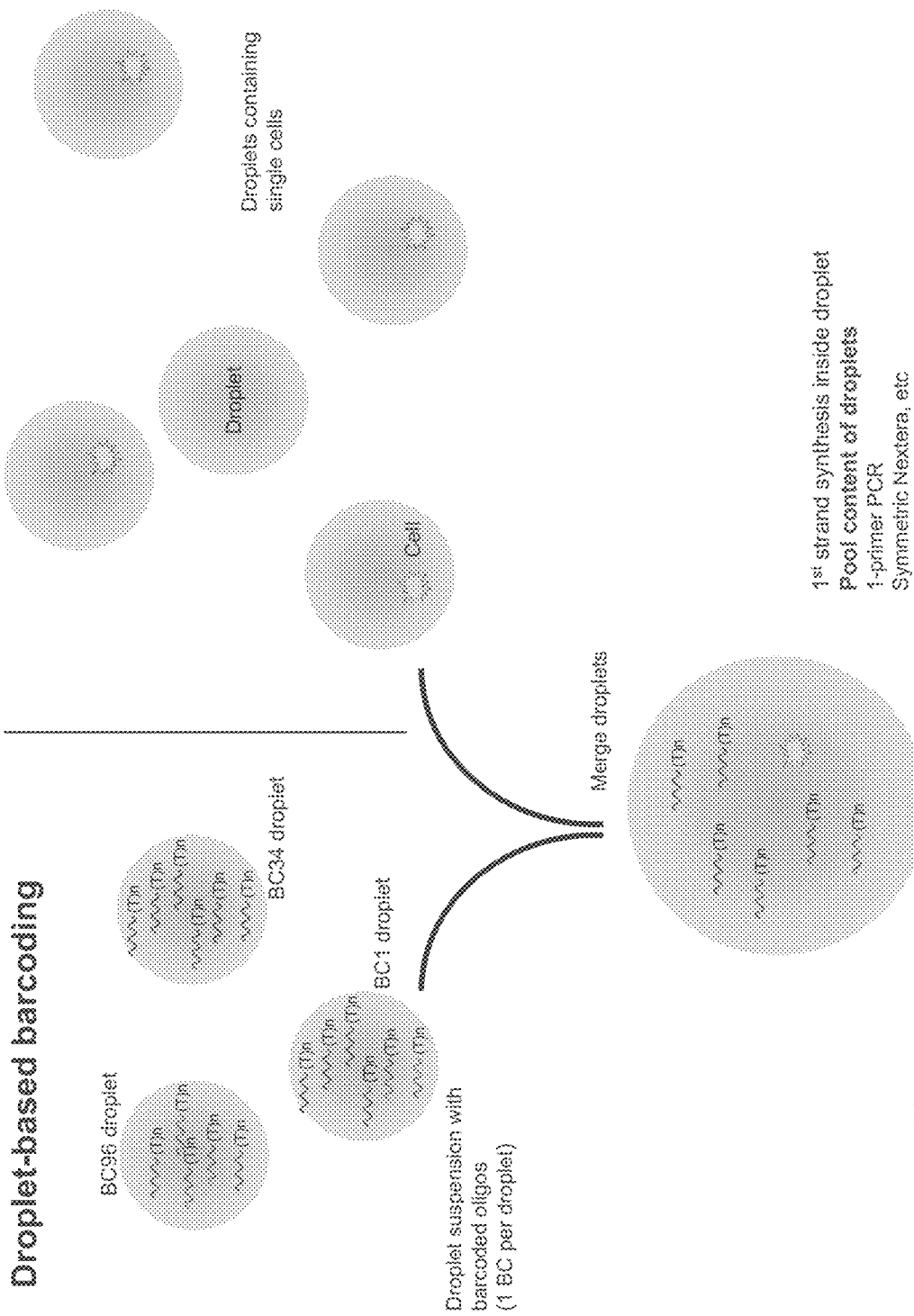
FIG. 11 is a schematic showing droplet-based barcoding according to one embodiment.

In some embodiments, sample and UMI barcoding can be performed by segregating individual cells into droplets. In some embodiments, the droplets are segregated from each other in an emulsion. In some embodiments, the droplets are formed and/or manipulated using a droplet actuator. In particular embodiments, one or more droplets comprise a different set of barcode-containing first strand synthesis primers. In some embodiments, each droplet comprise multitude of first strand synthesis primers, each of these primers have identical sequence including identical barcodes and the barcodes from one droplet differ from another droplet, while the remaining portion of the first strand synthesis primer remains the same between the droplets. Thus, in these embodiments, the barcodes act as identifier for the droplets as well as well as the single cell encompassed by the droplet. In particular embodiments, one or more droplets comprise a different set of UMI-containing first strand synthesis primers. Thus, each individual cell that is lysed in each droplet will be identifiable by the barcodes in each droplet. As illustrated in FIG. 11, droplet-based barcoding can be performed by merging droplets containing single cells with other droplets that comprise unique sets of barcodes. This format allows additional multiplexing beyond that available in a multiwall format. First strand synthesis and template switching is performed within each individual droplet. In some embodiments, two or more droplets can be merged prior to PCR. Additionally or alternatively, in some embodiments, droplets can be merged prior to tagmentation. Additionally or alternatively, in some embodiments, droplets can be merged after PCR and prior to tagmentation. For example, in some embodiments, after first strand synthesis is performed in individual droplets, the tagged cDNAs can be merged, thus pooling the cDNAs.

Figure 12:
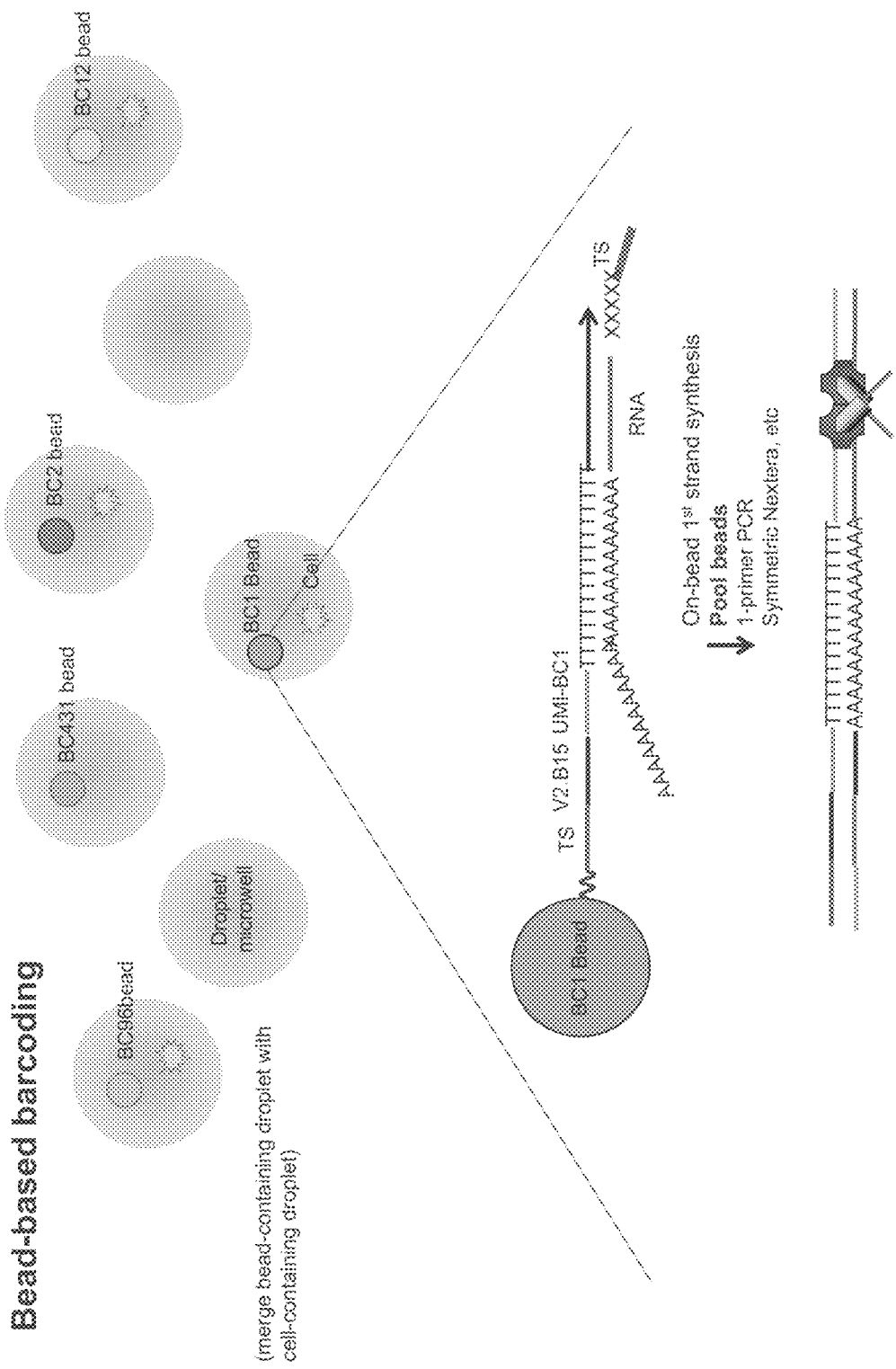
FIG. 12 is a schematic showing bead-based barcoding according to one embodiment. Figure discloses SEQ ID NOS 16, 20, 16, and 21, respectively, in order of appearance.
Figure 13:
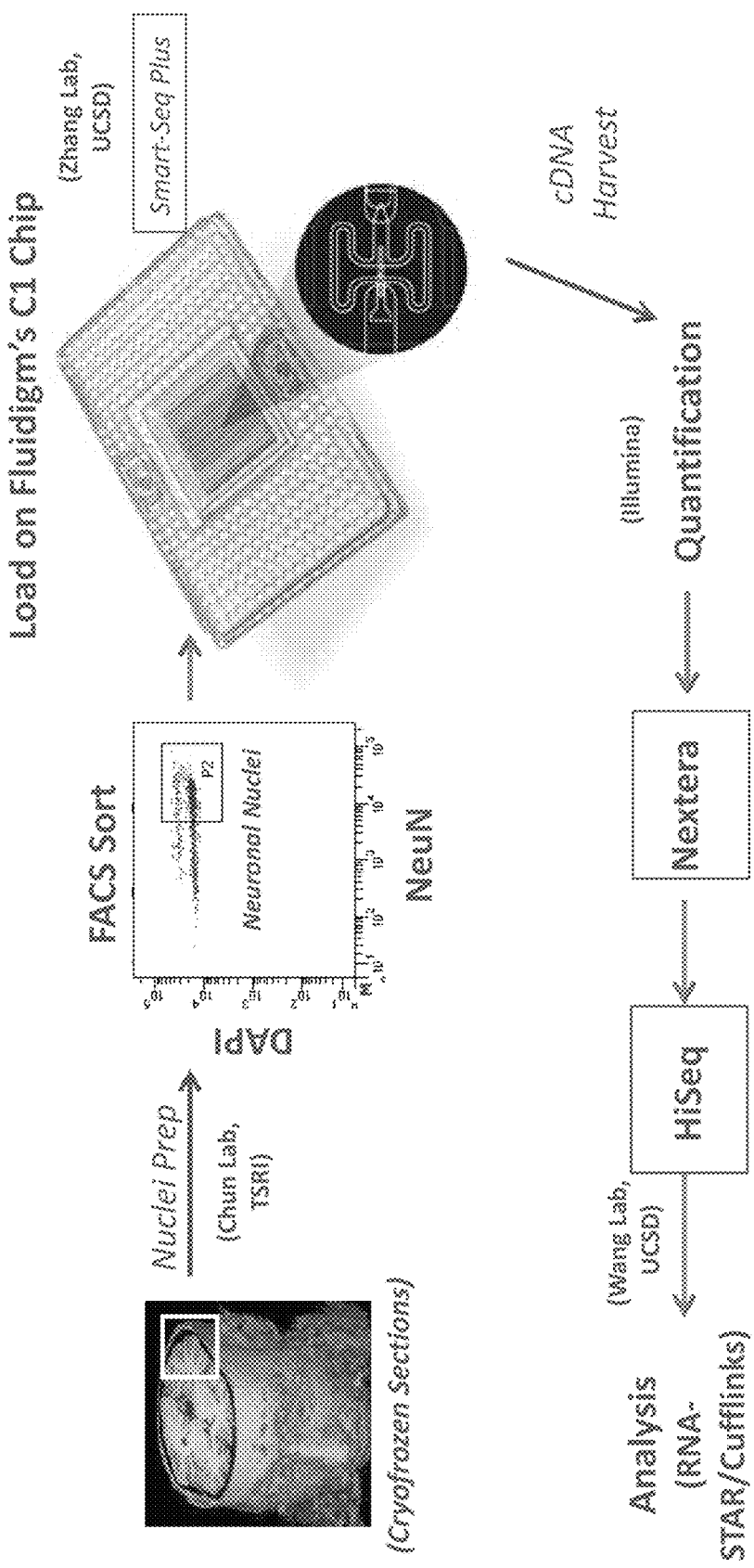
FIG. 13 is a schematic showing the single nuclei RNA-Sequencing workflow.
Figure 16:
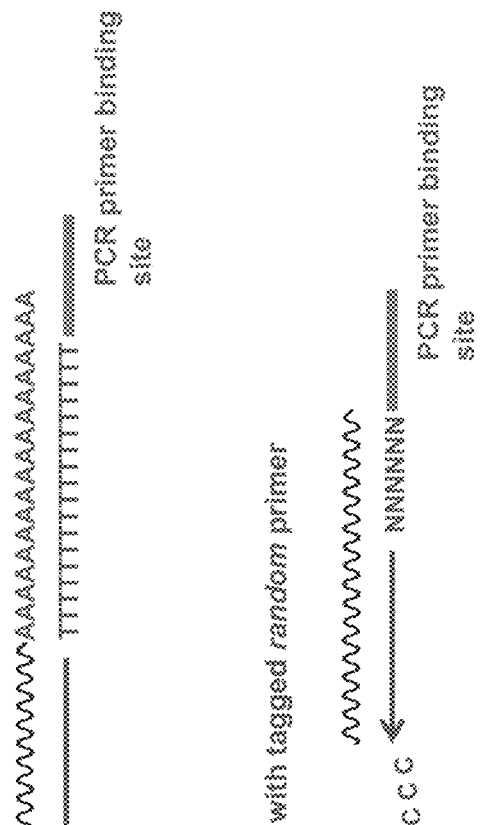
FIG. 16 is a schematic of cDNA synthesis was performed in the presence of a random primer in addition to the oligodT primer. Figure discloses SEQ ID NOS 14 and 22, respectively, in order of appearance.
Figure 18:
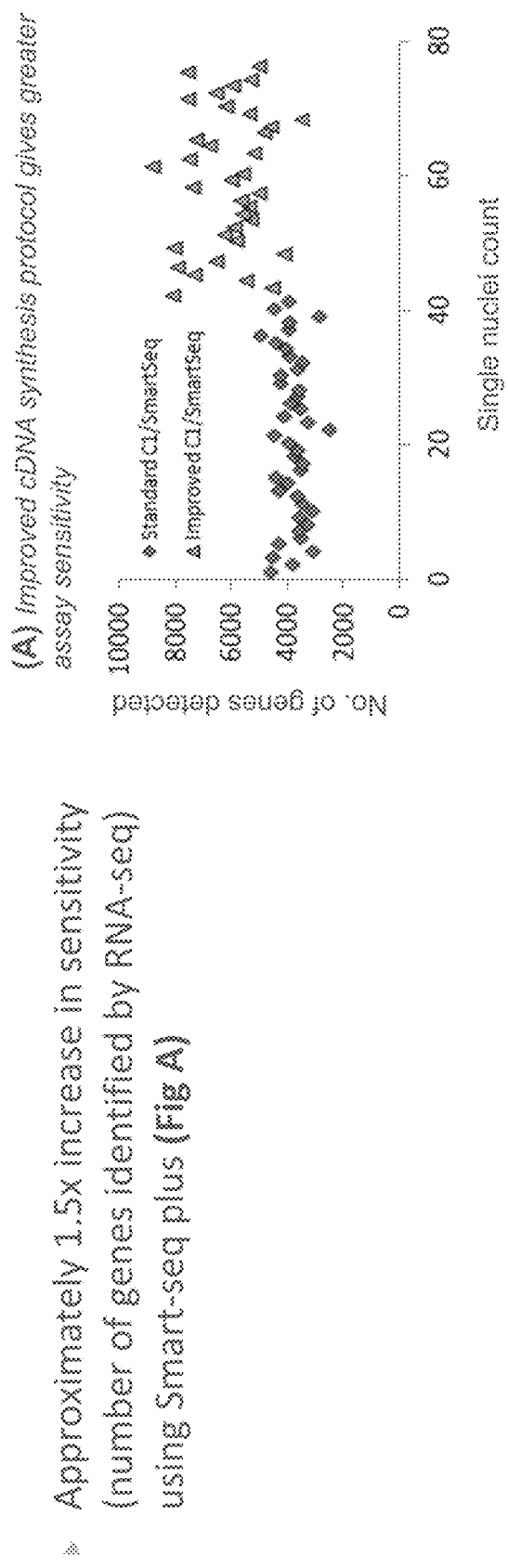
FIG. 18 shows the improved assay sensitivity of the SMART-Seq Plus over the SMART-seq method.

Similarly, in some embodiments, sample and UMI barcoding can be performed by segregating individual cells with beads that bear a UMI and/or barcode-tagged primer for first strand synthesis. In some embodiments, beads are segregated into droplets in an emulsion. In some embodiments, beads are segregated and manipulated using a droplet actuator. As illustrated in FIG. 12, bead-based barcoding can be performed by creating a set of beads, each bead bearing a unique set or sets of barcodes.

Whole Transcriptome Sequencing

Figure 9A:
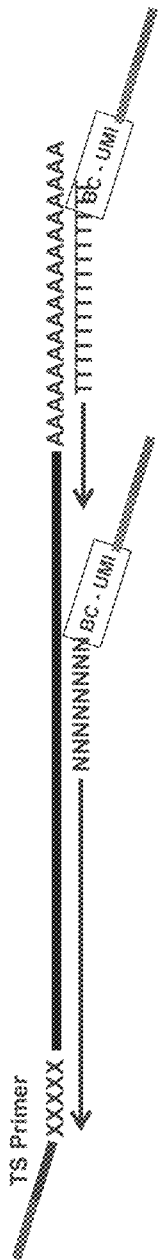
FIG. 9A is a schematic showing whole transcriptome analysis entailing first strand synthesis using randomers, according to one embodiment. Figure discloses SEQ ID NOS 14 and 19, respectively, in order of appearance.

In some embodiments, the methods provided herein can be utilized to perform whole transcriptome sequencing. In such embodiments, first strand synthesis is expanded using randomers. As illustrated in FIG. 9A, random priming expands the window of sequenceable fragments to anywhere along the length of the transcript where a randomer can hybridize and prime first strand synthesis. The randomers can include the same combinations of sample barcodes and unique molecular identifiers in addition to other adapter and primer binding sites, such as a transposome adapter sequence and/or template switching (TS) primer. Template switching and second strand synthesis can be performed as described above for oligo-dT primed cDNA synthesis. The resulting double stranded cDNAs can then be subjected to a tagmentation reaction as described above. The difference between use of randomers versus oligo-dT primers is that a complete, or substantially complete sequence of transcript can be obtained, rather than the 3' portion of the transcript. As shown in FIG. 6 (100 pg RNA), when gene expression was analyzed using either oligo-dT compared to mix of oligo-dT and randomers for first strand synthesis, a significant number of genes were detected and other metrics were obtained.

Figure 9B:
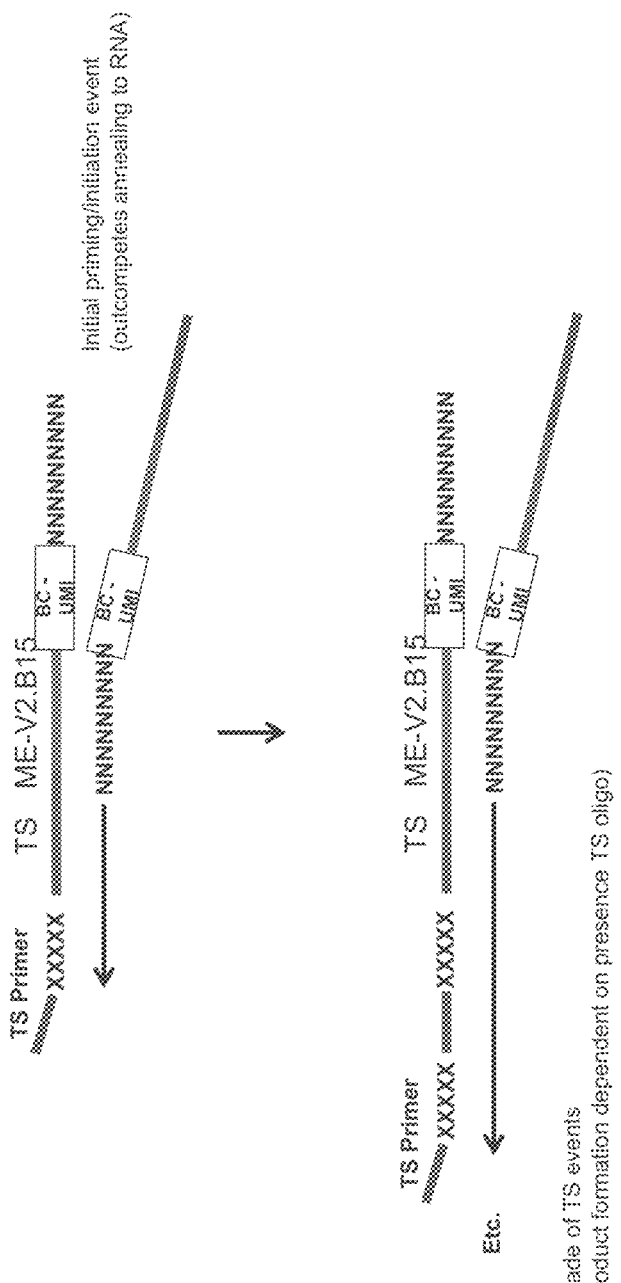
FIG. 9B is a schematic showing concatenation byproducts that may be produced when using randomers for first strand synthesis.

One type of byproduct that can occur when using randomers for priming first strand synthesis is concatenation byproducts. Specifically, in some situations, as illustrated in FIG. 9B, randomers may hybridize to other random primers, thus outcompeting annealing to RNA transcripts. The cDNA products that result may be further subjected to random priming and a cascade of template switching events can occur. This cascade can lead to formation of a byproduct of concatemers that may be dependent on the presence of the template switching oligonucleotide.

Figure 10:
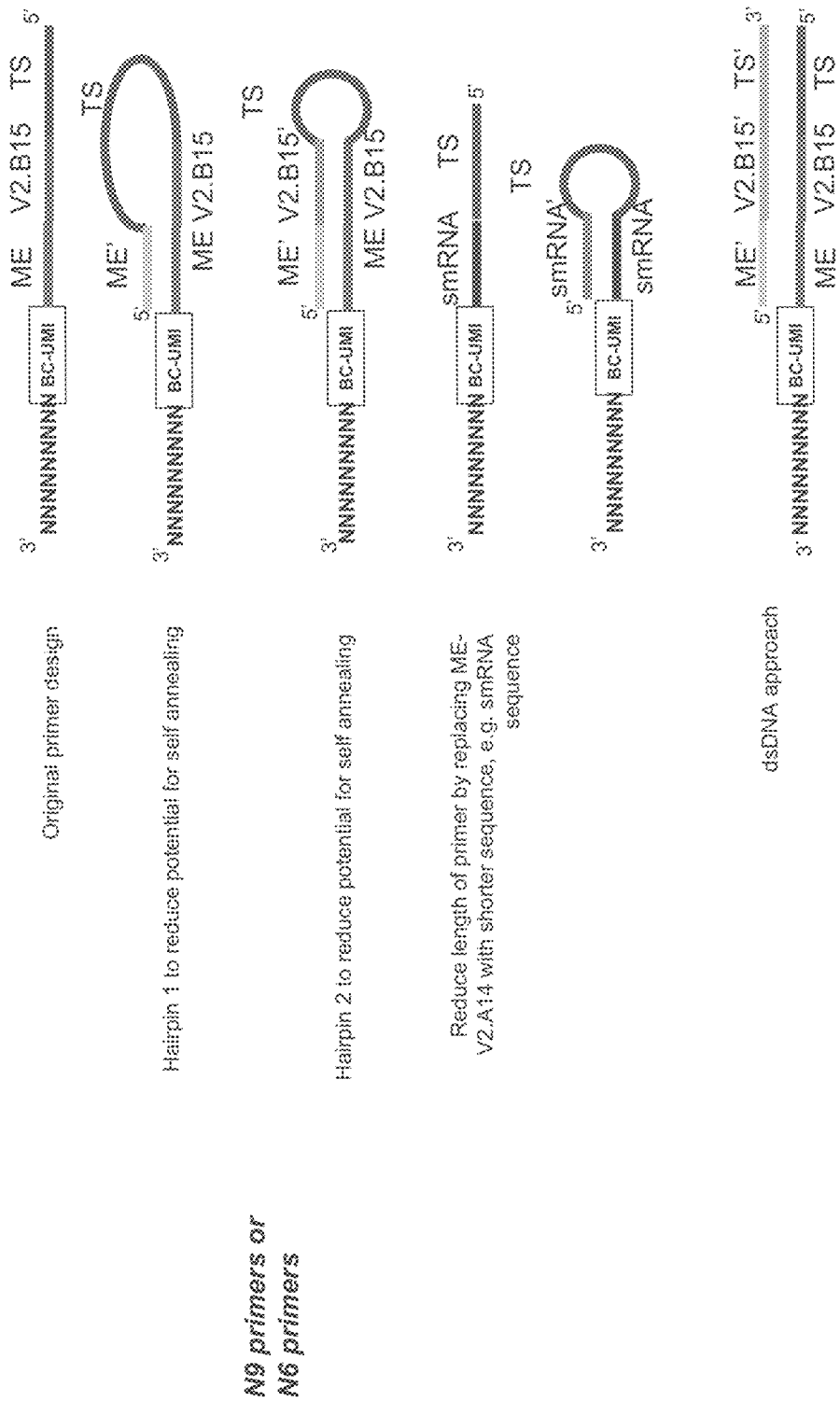
FIG. 10 shows various primer designs to reduce or avoid concatenation byproducts.

In order to reduce and/or minimize the formation of such byproducts, a variety of primer designs are presented herein which reduce the likelihood of byproduct formation. Exemplary designs are set forth in FIG. 10, although it will be appreciated that the scope of the primer compositions set forth herein extends beyond the examples set forth in the figure. In one embodiment, primers can be configured to form a hairpin to prevent or minimize randomer priming to any portion of the barcode, adapter or amplification primer binding regions. A double-stranded portion formed in the primer itself can thus out-compete randomer hybridization. In some embodiments, the double-stranded portion of the hairpin comprises the mosaic end (ME) sequence of the transposase adapter. Alternatively or additionally, in some embodiments, the double stranded portion can comprise some or all of the transposase adapter sequence, beyond the mosaic end sequence. In some embodiments, the adapter sequence can be completely replaced with a short RNA sequence, thus reducing the length of the primer and minimizing the potential for a randomer to hybridize to the primer. In some embodiments, a complement of the short RNA sequence is provided at or near the 5' end of the primer, thus enabling formation of a hairpin. In some embodiments, a double-stranded region is formed by annealing a complementary oligonucleotide to the adapter and/or primer portion, thus preventing or minimizing randomer priming to any portion of the barcode, adapter or amplification primer binding regions and thereby reducing or avoiding concatenation byproducts.

Randomer or Random Primer

As used herein, the terms "randomer" and "random primer: are used interchangeably. The term randomer refers to The random primers that can exhibit fourfold degeneracy at each position.

In some embodiments, the randomers comprises nucleic acid primers that are any of a variety of random sequence lengths, as known in the art. For example, the randomers can comprise a random sequence that is 3, 4, 5, 6, 7, 8, 10, 11, 12, 13, 14, 15, 16, 17, 18, 19, 20 or more nucleotides long. In certain embodiments, the plurality of random primers can comprise randomers of various lengths. In certain embodiments, the plurality of randomers can comprise randomers that are of equal length. In certain embodiments, the plurality of randomers can comprise a random sequence that is about 5 to about 18 nucleotides long. In some embodiments, the plurality of randomers comprises random hexamers. Random primers, and particularly random hexamers, are commercially available and widely used in amplification reactions such as Multiple Displacement Amplification (MDA), as exemplified by REPLI-g whole genome amplification kits (QIAGEN, Valencia, Calif.). It will be appreciated that any suitable length of randomers may be used in the methods and compositions presented herein.

Exemplary randomer sequences comprising a 3'-random sequence portion and a 5'-defined sequence portion are shown below:

```
                                        (SEQ ID NO: 6)
GTGTAGATCT CGGTGGTCGC CGTATCATTN NNNN (SEQ ID NO: 4)
GTGTAGATCT CGGTGGTCGC CGTATCATTN NNNNN (SEQ ID NO: 7)
GTGTAGATCT CGGTGGTCGC CGTATCATTN NNNNNN (SEQ ID NO: 8)
GTGTAGATCT CGGTGGTCGC CGTATCATTN NNNNNNN (SEQ ID NO: 9)
GTGTAGATCT CGGTGGTCGC CGTATCATTN NNNNNNNN (SEQ ID NO: 10)
ATCTCGTATG CCGTCTTCTG CTTGNNNNN (SEQ ID NO: 5)
ATCTCGTATG CCGTCTTCTG CTTGNNNNNN (SEQ ID NO: 11)
ATCTCGTATG CCGTCTTCTG CTTGNNNNNNN (SEQ ID NO: 12)
ATCTCGTATG CCGTCTTCTG CTTGNNNNNNNN (SEQ ID NO: 13)
ATCTCGTATG CCGTCTTCTG CTTGNNNNNNNNN
```

As used herein, the term "SMART-Seq Plus" means a method of preparing cDNA from RNA using a first strand synthesis primer comprising a first amplification primer binding site, a randomer comprising a first amplification primer binding site, and an oligonucleotide switching oligonucleotide that is partially complimentary to the first strand of the cDNA and comprises a second amplification primer binding site. In some embodiments, the first strand synthesis primer comprises an oligo(dT) portion.

Barcodes and UMIs

As used herein, the term "barcode" or "BC" refers to a nucleic acid tag that can be used to identify a sample or source of the nucleic acid material. Thus, where nucleic acid samples are derived from multiple sources, the nucleic acids in each nucleic acid sample can be tagged with different nucleic acid tags such that the source of the sample can be identified. Barcodes, also commonly referred to indexes, tags, and the like, are well known to those of skill in the art. Any suitable barcode or set of barcodes can be used, as known in the art and as exemplified by the disclosures of U.S. Pat. No. 8,053,192 and PCT Pub. WO05/068656, which are incorporated herein by reference in their entireties. Barcoding of single cells can be performed as described, for example in the disclosure of U.S. 2013/0274117, which is incorporated herein by reference in its entirety.

Nucleic acids from more than one source can incorporate a variable tag sequence. This tag sequence can be up to 100 nucleotides in length (base pairs if referring to double stranded molecules), preferably 1 to 10 nucleotides in length, most preferably 4, 5 or 6 nucleotides in length and comprises combinations of nucleotides. For example, in one embodiment, if six base-pairs are chosen to form the tag and a permutation of four different nucleotides used, then a total of 4096 nucleic acid anchors (e.g. hairpins), each with a unique 6 base tag can be made.

As used herein, the terms UMI, unique identifier, and unique molecular identifier refer to a unique nucleic acid sequence that is attached to each of a plurality of nucleic acid molecules. When incorporated into a nucleic acid molecule, for example during first strand cDNA synthesis, a UMI can be used to correct for subsequent amplification bias by directly counting unique molecular identifiers (UMIs) that are sequenced after amplification. The design, incorporation and application of UMIs can take place as known in the art, as exemplified by, for example, the disclosures of WO 2012/142213, Islam et al. Nat. Methods (2014) 11:163-166, and Kivioja, T. et al. Nat. Methods (2012) 9: 72-74, each of which is incorporated by reference in its entirety.

Tagmentation

As used herein, the term "tagmentation" refers to the modification of DNA by a transposome complex comprising transposase enzyme complexed with adaptors comprising transposon end sequence. Tagmentation results in the simultaneous fragmentation of the DNA and ligation of the adaptors to the 5' ends of both strands of duplex fragments. Following a purification step to remove the transposase enzyme, additional sequences can be added to the ends of the adapted fragments, for example by PCR, ligation, or any other suitable methodology known to those of skill in the art.

The method of the invention can use any transposase that can accept a transposase end sequence and fragment a target nucleic acid, attaching a transferred end, but not a non-transferred end. A "transposome" is comprised of at least a transposase enzyme and a transposase recognition site. In some such systems, termed "transposomes", the transposase can form a functional complex with a transposon recognition site that is capable of catalyzing a transposition reaction. The transposase or integrase may bind to the transposase recognition site and insert the transposase recognition site into a target nucleic acid in a process sometimes termed "tagmentation". In some such insertion events, one strand of the transposase recognition site may be transferred into the target nucleic acid.

In standard sample preparation methods, each template contains an adaptor at either end of the insert and often a number of steps are required to both modify the DNA or RNA and to purify the desired products of the modification reactions. These steps are performed in solution prior to the addition of the adapted fragments to a flowcell where they are coupled to the surface by a primer extension reaction that copies the hybridized fragment onto the end of a primer covalently attached to the surface. These 'seeding' templates then give rise to monoclonal clusters of copied templates through several cycles of amplification.

The number of steps required to transform DNA into adaptor-modified templates in solution ready for cluster formation and sequencing can be minimized by the use of transposase mediated fragmentation and tagging.

In some embodiments, transposon based technology can be utilized for fragmenting DNA, for example as exemplified in the workflow for Nextera™ DNA sample preparation kits (Illumina, Inc.) wherein genomic DNA can be fragmented by an engineered transposome that simultaneously fragments and tags input DNA ("tagmentation") thereby creating a population of fragmented nucleic acid molecules which comprise unique adapter sequences at the ends of the fragments.

Some embodiments can include the use of a hyperactive Tn5 transposase and a Tn5-type transposase recognition site (Goryshin and Reznikoff, J. Biol. Chem., 273:7367 (1998)), or MuA transposase and a Mu transposase recognition site comprising R1 and R2 end sequences (Mizuuchi, K., Cell, 35: 785, 1983; Savilahti, H, et al., EMBO J., 14: 4893, 1995). An exemplary transposase recognition site that forms a complex with a hyperactive Tn5 transposase (e.g., EZ-Tn5™ Transposase, Epicentre Biotechnologies, Madison, Wis.).

More examples of transposition systems that can be used with certain embodiments provided herein include *Staphylococcus aureus* Tn552 (Colegio et al., J. Bacteriol., 183: 2384-8, 2001; Kirby C et al., Mol. Microbiol., 43: 173-86, 2002), Ty1 (Devine & Boeke, Nucleic Acids Res., 22: 3765-72, 1994 and International Publication WO 95/23875), Transposon Tn7 (Craig, N L, Science. 271: 1512, 1996; Craig, N L, Review in: Curr Top Microbiol Immunol., 204:27-48, 1996), Tn/O and IS10 (Kleckner N, et al., Curr Top Microbiol Immunol., 204:49-82, 1996), Mariner transposase (Lampe D J, et al., EMBO J., 15: 5470-9, 1996), Tc1 (Plasterk R H, Curr. Topics Microbiol. Immunol., 204: 125-43, 1996), P Element (Gloor, G B, Methods Mol. Biol., 260: 97-114, 2004), Tn3 (Ichikawa & Ohtsubo, J Biol. Chem. 265:18829-32, 1990), bacterial insertion sequences (Ohtsubo & Sekine, Curr. Top. Microbiol. Immunol. 204: 1-26, 1996), retroviruses (Brown, et al., Proc Natl Acad Sci USA, 86:2525-9, 1989), and retrotransposon of yeast (Boeke & Corces, Annu Rev Microbiol. 43:403-34, 1989). More examples include IS5, Tn10, Tn903, IS911, and engineered versions of transposase family enzymes (Zhang et al., (2009) PLoS Genet. 5:e1000689. Epub 2009 Oct. 16; Wilson C. et al (2007) J. Microbiol. Methods 71:332-5).

Briefly, a "transposition reaction" is a reaction wherein one or more transposons are inserted into target nucleic acids at random sites or almost random sites. Essential components in a transposition reaction are a transposase and DNA oligonucleotides that exhibit the nucleotide sequences of a transposon, including the transferred transposon sequence and its complement (i.e., the non-transferred transposon end sequence) as well as other components needed to form a functional transposition or transposome complex. The DNA oligonucleotides can further comprise additional sequences (e.g., adaptor or primer sequences) as needed or desired. Briefly, in vitro transposition can be initiated by contacting a transposome complex and a target DNA. Exemplary transposition procedures and systems that can be readily adapted for use with the transposases of the present disclosure are described, for example, in WO 10/048605; US 2012/0301925; US 2013/0143774, each of which is incorporated herein by reference in its entirety.

The adapters that are added to the 5' and/or 3' end of a nucleic acid can comprise a universal sequence. A universal sequence is a region of nucleotide sequence that is common to, i.e., shared by, two or more nucleic acid molecules. Optionally, the two or more nucleic acid molecules also have regions of sequence differences. Thus, for example, the 5' adapters can comprise identical or universal nucleic acid sequences and the 3' adapters can comprise identical or universal sequences. A universal sequence that may be present in different members of a plurality of nucleic acid molecules can allow the replication or amplification of multiple different sequences using a single universal primer that is complementary to the universal sequence. Some universal primer sequences used in examples presented herein include the V2.A14 and V2.B15 Nextera™ sequences. However, it will be readily appreciated that any suitable adapter sequence can be utilized in the methods and compositions presented herein. For example, Tn5 Mosaic End Sequence A14 (Tn5MEA) and/or Tn5 Mosaic End Sequence B15 (Tn5MEB), including the complementary non transferred sequence (NTS) as set forth below, can be used in the methods provided herein.

Tn5MEA:
(SEQ ID NO: 1)
5'-TCGTCGGCAGCGTCAGATGTGTATAAGAGACAG-3'

Tn5MEB:
(SEQ ID NO: 2)
5'-GTCTCGTGGGCTCGGAGATGTGTATAAGAGACAG-3'

Tn5 NTS:
(SEQ ID NO: 3)
5'-CTGTCTCTTATACACATCT-3'

Barcodes and UMIs in Droplets

In some embodiments, primers bearing sample barcodes can be in solution. Additionally or alternatively, primers bearing UMI sequences can be in solution. For example, the solid support can be one or more droplets. Thus, in certain embodiments, a plurality of droplets can be presented, wherein each droplet in the plurality bears a unique sample barcode and/or UMI sequences, each of which are unique to a molecule. Thus, a person of ordinary skill in the art will understand that in some embodiments, the barcodes are unique to a droplet and the UMI are unique to a molecule such that the UMI are repeated many times within a collection of droplets. In some embodiments, individual cells are contacted with a droplet having a unique set of sample barcodes and/or UMI sequences in order to identify the individual cell. In some embodiments, lysates from individual cells are contacted with a droplet having a unique set of sample barcodes and/or UMI sequences in order to identify the individual cell lysates. In some embodiments, purified nucleic acid from individual cells are contacted with a droplet having a unique set of sample barcodes and/or UMI sequences in order to identify the purified nucleic acid from the individual cell.

Any suitable system for forming and manipulating droplets can be used in the embodiments presented herein where each droplet in a plurality of droplets bears a unique set of sample barcodes and/or UMI sequences. For example, a droplet actuator may be used.

"Droplet Actuator" means a device for manipulating droplets. For examples of droplet actuators, see Pamula et al., U.S. Pat. No. 6,911,132, entitled "Apparatus for Manipulating Droplets by Electrowetting-Based Techniques," issued on Jun. 28, 2005; Pamula et al., U.S. Patent Pub. No. 20060194331, entitled "Apparatuses and Methods for Manipulating Droplets on a Printed Circuit Board," published on Aug. 31, 2006; Pollack et al., International Patent Pub. No. WO/2007/120241, entitled "Droplet-Based Biochemistry," published on Oct. 25, 2007; Shenderov, U.S. Pat. No. 6,773,566, entitled "Electrostatic Actuators for Microfluidics and Methods for Using Same," issued on Aug. 10, 2004; Shenderov, U.S. Pat. No. 6,565,727, entitled "Actuators for Microfluidics Without Moving Parts," issued on May 20, 2003; Kim et al., U.S. Patent Pub. No. 20030205632, entitled "Electrowetting-driven Micropumping," published on Nov. 6, 2003; Kim et al., U.S. Patent Pub. No. 20060164490, entitled "Method and Apparatus for Promoting the Complete Transfer of Liquid Drops from a Nozzle," published on Jul. 27, 2006; Kim et al., U.S. Patent Pub. No. 20070023292, entitled "Small Object Moving on Printed Circuit Board," published on Feb. 1, 2007; Shah et al., U.S. Patent Pub. No. 20090283407, entitled "Method for Using Magnetic Particles in Droplet Microfluidics," published on Nov. 19, 2009; Kim et al., U.S. Patent Pub. No. 20100096266, entitled "Method and Apparatus for Real-time Feedback Control of Electrical Manipulation of Droplets on Chip," published on Apr. 22, 2010; Velev, U.S. Pat. No. 7,547,380, entitled "Droplet Transportation Devices and Methods Having a Fluid Surface," issued on Jun. 16, 2009; Sterling et al., U.S. Pat. No. 7,163,612, entitled "Method, Apparatus and Article for Microfluidic Control via Electrowetting, for Chemical, Biochemical and Biological Assays and the Like," issued on Jan. 16, 2007; Becker et al., U.S. Pat. No. 7,641,779, entitled "Method and Apparatus for Programmable Fluidic Processing," issued on Jan. 5, 2010; Becker et al., U.S. Pat. No. 6,977,033, entitled "Method and Apparatus for Programmable Fluidic Processing," issued on Dec. 20, 2005; Decre et al., U.S. Pat. No. 7,328,979, entitled "System for Manipulation of a Body of Fluid," issued on Feb. 12, 2008; Yamakawa et al., U.S. Patent Pub. No. 20060039823, entitled "Chemical Analysis Apparatus," published on Feb. 23, 2006; Wu, U.S. Patent Pub. No. 20110048951, entitled "Digital Microfluidics Based Apparatus for Heat-exchanging Chemical Processes," published on Mar. 3, 2011; Fouillet et al., U.S. Patent Pub. No. 20090192044, entitled "Electrode Addressing Method," published on Jul. 30, 2009; Fouillet et al., U.S. Pat. No. 7,052,244, entitled "Device for Displacement of Small Liquid Volumes Along a Micro-catenary Line by Electrostatic Forces," issued on May 30, 2006; Marchand et al., U.S. Patent Pub. No. 20080124252, entitled "Droplet Microreactor," published on May 29, 2008; Adachi et al., U.S. Patent Pub. No. 20090321262, entitled "Liquid Transfer Device," published on Dec. 31, 2009; Roux et al., U.S. Patent Pub. No. 20050179746, entitled "Device for Controlling the Displacement of a Drop Between Two or Several Solid Substrates," published on Aug. 18, 2005; and Dhindsa et al., "Virtual Electrowetting Channels: Electronic Liquid Transport with Continuous Channel Functionality," Lab Chip, 10:832-836 (2010), the entire disclosures of which are incorporated herein by reference. Certain droplet actuators will include one or more substrates arranged with a droplet operations gap therebetween and electrodes associated with (e.g., layered on, attached to, and/or embedded in) the one or more substrates and arranged to conduct one or more droplet operations. For example, certain droplet actuators will include a base (or bottom) substrate, droplet operations electrodes associated with the substrate, one or more dielectric layers atop the substrate and/or electrodes, and optionally one or more hydrophobic layers atop the substrate, dielectric layers and/or the electrodes forming a droplet operations surface. A top substrate may also be provided, which is separated from the droplet operations surface by a gap, commonly referred to as a droplet operations gap. Various electrode arrangements on the top and/or bottom substrates are discussed in the above-referenced patents and applications and certain novel electrode arrangements are discussed in the description of the present disclosure. During droplet operations it is preferred that droplets remain in continuous contact or frequent contact with a ground or reference electrode. A ground or reference electrode may be associated with the top substrate facing the gap, the bottom substrate facing the gap, in the gap. Where electrodes are provided on both substrates, electrical contacts for coupling the electrodes to a droplet actuator instrument for controlling or monitoring the electrodes may be associated with one or both plates. In some cases, electrodes on one substrate are electrically coupled to the other substrate so that only one substrate is in contact with the droplet actuator. In one embodiment, a conductive material (e.g., an epoxy, such as MASTER BOND™ Polymer System EP79, available from Master Bond, Inc., Hackensack, N.J.) provides the electrical connection between electrodes on one substrate and electrical paths on the other substrates, e.g., a ground electrode on a top substrate may be coupled to an electrical path on a bottom substrate by such a conductive material. Where multiple substrates are used, a spacer may be provided between the substrates to determine the height of the gap therebetween and define on-actuator dispensing reservoirs. The spacer height may, for example, be at least about 5 μm, 100 μm, 200 μm, 250 μm, 275 μm or more. Alternatively or additionally the spacer height may be at most about 600 μm, 400 μm, 350 μm, 300 μm, or less. The spacer may, for example, be formed of a layer of projections form the top or bottom substrates, and/or a material inserted between the top and bottom substrates. One or more openings may be provided in the one or more substrates for forming a fluid path through which liquid may be delivered into the droplet operations gap. The one or more openings may in some cases be aligned for interaction with one or more electrodes, e.g., aligned such that liquid flowed through the opening will come into sufficient proximity with one or more droplet operations electrodes to permit a droplet operation to be effected by the droplet operations electrodes using the liquid. The base (or bottom) and top substrates may in some cases be formed as one integral component. One or more reference electrodes may be provided on the base (or bottom) and/or top substrates and/or in the gap. Examples of reference electrode arrangements are provided in the above referenced patents and patent applications. In various embodiments, the manipulation of droplets by a droplet actuator may be electrode mediated, e.g., electrowetting mediated or dielectrophoresis mediated or Coulombic force mediated. Examples of other techniques for controlling droplet operations that may be used in the droplet actuators of the present disclosure include using devices that induce hydrodynamic fluidic pressure, such as those that operate on the basis of mechanical principles (e.g. external syringe pumps, pneumatic membrane pumps, vibrating membrane pumps, vacuum devices, centrifugal forces, piezoelectric/ultrasonic pumps and acoustic forces); electrical or magnetic principles (e.g. electroosmotic flow, electrokinetic pumps, ferrofluidic plugs, electrohydrodynamic pumps, attraction or repulsion using magnetic forces and magnetohydrodynamic pumps); thermodynamic principles (e.g. gas bubble generation/phase-change-induced volume expansion); other kinds of surface-wetting principles (e.g. electrowetting, and optoelectrowetting, as well as chemically, thermally, structurally and radioactively induced surface-tension gradients); gravity; surface tension (e.g., capillary action); electrostatic forces (e.g., electroosmotic flow); centrifugal flow (substrate disposed on a compact disc and rotated); magnetic forces (e.g., oscillating ions causes flow); magnetohydrodynamic forces; and vacuum or pressure differential. In certain embodiments, combinations of two or more of the foregoing techniques may be employed to conduct a droplet operation in a droplet actuator of the present disclosure. Similarly, one or more of the foregoing may be used to deliver liquid into a droplet operations gap, e.g., from a reservoir in another device or from an external reservoir of the droplet actuator (e.g., a reservoir associated with a droplet actuator substrate and a flow path from the reservoir into the droplet operations gap). Droplet operations surfaces of certain droplet actuators of the present disclosure may be made from hydrophobic materials or may be coated or treated to make them hydrophobic. For example, in some cases some portion or all of the droplet operations surfaces may be derivatized with low surface-energy materials or chemistries, e.g., by deposition or using in situ synthesis using compounds such as poly- or per-fluorinated compounds in solution or polymerizable monomers. Examples include TEFLON® AF (available from DuPont, Wilmington, Del.), members of the cytop family of materials, coatings in the FLUOROPEL® family of hydrophobic and superhydrophobic coatings (available from Cytonix Corporation, Beltsville, Md.), silane coatings, fluorosilane coatings, hydrophobic phosphonate derivatives (e.g., those sold by Aculon, Inc), and NOVEC™ electronic coatings (available from 3M Company, St. Paul, Minn.), other fluorinated monomers for plasma-enhanced chemical vapor deposition (PECVD), and organosiloxane (e.g., SiOC) for PECVD. In some cases, the droplet operations surface may include a hydrophobic coating having a thickness ranging from about 10 nm to about 1,000 nm. Moreover, in some embodiments, the top substrate of the droplet actuator includes an electrically conducting organic polymer, which is then coated with a hydrophobic coating or otherwise treated to make the droplet operations surface hydrophobic. For example, the electrically conducting organic polymer that is deposited onto a plastic substrate may be poly(3,4-ethylenedioxythiophene)poly(styrenesulfonate) (PEDOT: PSS). Other examples of electrically conducting organic polymers and alternative conductive layers are described in Pollack et al., International Patent Pub. No. WO/2011/002957, entitled "Droplet Actuator Devices and Methods," published on Jan. 6, 2011, the entire disclosure of which is incorporated herein by reference. One or both substrates may be fabricated using a printed circuit board (PCB), glass, indium tin oxide (ITO)-coated glass, and/or semiconductor materials as the substrate. When the substrate is ITO-coated glass, the ITO coating is preferably a thickness of at least about 20 nm, 50 nm, 75 nm, 100 nm or more. Alternatively or additionally the thickness can be at most about 200 nm, 150 nm, 125 nm or less. In some cases, the top and/or bottom substrate includes a PCB substrate that is coated with a dielectric, such as a polyimide dielectric, which may in some cases also be coated or otherwise treated to make the droplet operations surface hydrophobic. When the substrate includes a PCB, the following materials are examples of suitable materials: MITSUI™ BN-300 (available from MITSUI Chemicals America, Inc., San Jose Calif.); ARLON™ 11N (available from Arlon, Inc, Santa Ana, Calif.).; NELCO® N4000-6 and N5000-30/32 (available from Park Electrochemical Corp., Melville, N.Y.); ISOLA™ FR406 (available from Isola Group, Chandler, Ariz.), especially IS620; fluoropolymer family (suitable for fluorescence detection since it has low background fluorescence); polyimide family; polyester; polyethylene naphthalate; polycarbonate; polyetheretherketone; liquid crystal polymer; cyclo-olefin copolymer (COC); cyclo-olefin polymer (COP); aramid; THERMOUNT® nonwoven aramid reinforcement (available from DuPont, Wilmington, Del.); NOMEX® brand fiber (available from DuPont, Wilmington, Del.); and paper. Various materials are also suitable for use as the dielectric component of the substrate. Examples include: vapor deposited dielectric, such as PARYLENE™ C (especially on glass), PARYLENE™ N, and PARYLENE™ HT (for high temperature, ~300° C.) (available from Parylene Coating Services, Inc., Katy, Tex.); TEFLON® AF coatings; cytop; soldermasks, such as liquid photoimageable soldermasks (e.g., on PCB) like TAIYO™ PSR4000 series, TAIYO™ PSR and AUS series (available from Taiyo America, Inc. Carson City, Nev.) (good thermal characteristics for applications involving thermal control), and PROBIMER™ 8165 (good thermal characteristics for applications involving thermal control (available from Huntsman Advanced Materials Americas Inc., Los Angeles, Calif.); dry film soldermask, such as those in the VACREL® dry film soldermask line (available from DuPont, Wilmington, Del.);

film dielectrics, such as polyimide film (e.g., KAPTON® polyimide film, available from DuPont, Wilmington, Del.), polyethylene, and fluoropolymers (e.g., FEP), polytetrafluoroethylene; polyester; polyethylene naphthalate; cyclo-olefin copolymer (COC); cyclo-olefin polymer (COP); any other PCB substrate material listed above; black matrix resin; polypropylene; and black flexible circuit materials, such as DuPont™ Pyralux® HXC and DuPont™ Kapton® MBC (available from DuPont, Wilmington, Del.). Droplet transport voltage and frequency may be selected for performance with reagents used in specific assay protocols. Design parameters may be varied, e.g., number and placement of on-actuator reservoirs, number of independent electrode connections, size (volume) of different reservoirs, placement of magnets/bead washing zones, electrode size, inter-electrode pitch, and gap height (between top and bottom substrates) may be varied for use with specific reagents, protocols, droplet volumes, etc. In some cases, a substrate of the present disclosure may be derivatized with low surface-energy materials or chemistries, e.g., using deposition or in situ synthesis using poly- or per-fluorinated compounds in solution or polymerizable monomers. Examples include TEFLON® AF coatings and FLUOROPEL® coatings for dip or spray coating, other fluorinated monomers for plasma-enhanced chemical vapor deposition (PECVD), and organosiloxane (e.g., SiOC) for PECVD. Additionally, in some cases, some portion or the entire droplet operations surface may be coated with a substance for reducing background noise, such as background fluorescence from a PCB substrate. For example, the noise-reducing coating may include a black matrix resin, such as the black matrix resins available from Toray industries, Inc., Japan. Electrodes of a droplet actuator are typically controlled by a controller or a processor, which is itself provided as part of a system, which may include processing functions as well as data and software storage and input and output capabilities. Reagents may be provided on the droplet actuator in the droplet operations gap or in a reservoir fluidly coupled to the droplet operations gap. The reagents may be in liquid form, e.g., droplets, or they may be provided in a reconstitutable form in the droplet operations gap or in a reservoir fluidly coupled to the droplet operations gap. Reconstitutable reagents may typically be combined with liquids for reconstitution. An example of reconstitutable reagents suitable for use with the methods and apparatus set forth herein includes those described in Meathrel et al., U.S. Pat. No. 7,727,466, entitled "Disintegratable Films for Diagnostic Devices," issued on Jun. 1, 2010, the entire disclosure of which is incorporated herein by reference.

"Activate," with reference to one or more electrodes, means affecting a change in the electrical state of the one or more electrodes which, in the presence of a droplet, results in a droplet operation. Activation of an electrode can be accomplished using alternating current (AC) or direct current (DC). Any suitable voltage may be used. For example, an electrode may be activated using a voltage which is greater than about 150 V, or greater than about 200 V, or greater than about 250 V, or from about 275 V to about 1000 V, or about 300 V. Where an AC signal is used, any suitable frequency may be employed. For example, an electrode may be activated using an AC signal having a frequency from about 1 Hz to about 10 MHz, or from about 10 Hz to about 60 Hz, or from about 20 Hz to about 40 Hz, or about 30 Hz.

"Bead," with respect to beads on a droplet actuator, means any bead or particle that is capable of interacting with a droplet on or in proximity with a droplet actuator. Beads may be any of a wide variety of shapes, such as spherical, generally spherical, egg shaped, disc shaped, cubical, amorphous and other three dimensional shapes. The bead may, for example, be capable of being subjected to a droplet operation in a droplet on a droplet actuator or otherwise configured with respect to a droplet actuator in a manner which permits a droplet on the droplet actuator to be brought into contact with the bead on the droplet actuator and/or off the droplet actuator. Beads may be provided in a droplet, in a droplet operations gap, or on a droplet operations surface. Beads may be provided in a reservoir that is external to a droplet operations gap or situated apart from a droplet operations surface, and the reservoir may be associated with a flow path that permits a droplet including the beads to be brought into a droplet operations gap or into contact with a droplet operations surface. Beads may be manufactured using a wide variety of materials, including for example, resins, and polymers. The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead, a portion of a bead, or only one component of a bead. The remainder of the bead may include, among other things, polymeric material, coatings, and moieties which permit attachment of an assay reagent. Examples of suitable beads include flow cytometry microbeads, polystyrene microparticles and nanoparticles, functionalized polystyrene microparticles and nanoparticles, coated polystyrene microparticles and nanoparticles, silica microbeads, fluorescent microspheres and nanospheres, functionalized fluorescent microspheres and nanospheres, coated fluorescent microspheres and nanospheres, color dyed microparticles and nanoparticles, magnetic microparticles and nanoparticles, superparamagnetic microparticles and nanoparticles (e.g., DYNABEADS® particles, available from Invitrogen Group, Carlsbad, Calif.), fluorescent microparticles and nanoparticles, coated magnetic microparticles and nanoparticles, ferromagnetic microparticles and nanoparticles, coated ferromagnetic microparticles and nanoparticles, and those described in Watkins et al., U.S. Patent Pub. No. 20050260686, entitled "Multiplex Flow Assays Preferably with Magnetic Particles as Solid Phase," published on Nov. 24, 2005; Chandler., U.S. Patent Pub. No. 20030132538, entitled "Encapsulation of Discrete Quanta of Fluorescent Particles," published on Jul. 17, 2003; Chandler et al., U.S. Patent Pub. No. 20050118574, entitled "Multiplexed Analysis of Clinical Specimens Apparatus and Method," published on Jun. 2, 2005; Chandler et al., U.S. Patent Pub. No. 20050277197, entitled "Microparticles with Multiple Fluorescent Signals and Methods of Using Same," published on Dec. 15, 2005; and Chandler et al., U.S. Patent Pub. No. 20060159962, entitled "Magnetic Microspheres for use in Fluorescence-based Applications," published on Jul. 20, 2006, the entire disclosures of which are incorporated herein by reference for their teaching concerning beads and magnetically responsive materials and beads. Beads may be pre-coupled with a biomolecule or other substance that is able to bind to and form a complex with a biomolecule. Beads may be pre-coupled with an antibody, protein or antigen, DNA/RNA probe or any other molecule with an affinity for a desired target. Examples of droplet actuator techniques for immobilizing magnetically responsive beads and/or non-magnetically responsive beads and/or conducting droplet operations protocols using beads are described in Pollack et al., U.S. Patent Pub. No. 20080053205, entitled "Droplet-Based Particle Sorting," published on Mar. 6, 2008; U.S. Patent App. No. 61/039,183, entitled "Multiplexing Bead Detection in a Single Droplet," filed on Mar. 25, 2008; Pamula et al., U.S. Patent App. No. 61/047,789, entitled "Droplet Actuator Devices and Droplet Operations Using Beads," filed on Apr. 25, 2008; U.S. Patent App. No. 61/086,183, entitled "Droplet Actuator Devices and Methods for Manipulating Beads," filed on Aug. 5, 2008; Eckhardt et al., International Patent Pub. No. WO/2008/098236, entitled "Droplet Actuator Devices and Methods Employing Magnetic Beads," published on Aug. 14, 2008; Grichko et al., International Patent Pub. No. WO/2008/134153, entitled "Bead-based Multiplexed Analytical Methods and Instrumentation," published on Nov. 6, 2008; Eckhardt et al., International Patent Pub. No. WO/2008/116221, "Bead Sorting on a Droplet Actuator," published on Sep. 25, 2008; and Eckhardt et al., International Patent Pub. No. WO/2007/120241, entitled "Droplet-based Biochemistry," published on Oct. 25, 2007, the entire disclosures of which are incorporated herein by reference. Bead characteristics may be employed in the multiplexing aspects of the present disclosure. Examples of beads having characteristics suitable for multiplexing, as well as methods of detecting and analyzing signals emitted from such beads, may be found in Whitman et al., U.S. Patent Pub. No. 20080305481, entitled "Systems and Methods for Multiplex Analysis of PCR in Real Time," published on Dec. 11, 2008; Roth, U.S. Patent Pub. No. 20080151240, "Methods and Systems for Dynamic Range Expansion," published on Jun. 26, 2008; Sorensen et al., U.S. Patent Pub. No. 20070207513, entitled "Methods, Products, and Kits for Identifying an Analyte in a Sample," published on Sep. 6, 2007; Roth, U.S. Patent Pub. No. 20070064990, entitled "Methods and Systems for Image Data Processing," published on Mar. 22, 2007; Chandler et al., U.S. Patent Pub. No. 20060159962, entitled "Magnetic Microspheres for use in Fluorescence-based Applications," published on Jul. 20, 2006; Chandler et al., U.S. Patent Pub. No. 20050277197, entitled "Microparticles with Multiple Fluorescent Signals and Methods of Using Same," published on Dec. 15, 2005; and Chandler et al., U.S. Patent Publication No. 20050118574, entitled "Multiplexed Analysis of Clinical Specimens Apparatus and Method," published on Jun. 2, 2005, the entire disclosures of which are incorporated herein by reference.

"Droplet" means a volume of liquid on a droplet actuator. Typically, a droplet is at least partially bounded by a filler fluid. For example, a droplet may be completely surrounded by a filler fluid or may be bounded by filler fluid and one or more surfaces of the droplet actuator. As another example, a droplet may be bounded by filler fluid, one or more surfaces of the droplet actuator, and/or the atmosphere. As yet another example, a droplet may be bounded by filler fluid and the atmosphere. Droplets may, for example, be aqueous or non-aqueous or may be mixtures or emulsions including aqueous and non-aqueous components. Droplets may take a wide variety of shapes; nonlimiting examples include generally disc shaped, slug shaped, truncated sphere, ellipsoid, spherical, partially compressed sphere, hemispherical, ovoid, cylindrical, combinations of such shapes, and various shapes formed during droplet operations, such as merging or splitting or formed as a result of contact of such shapes with one or more surfaces of a droplet actuator. For examples of droplet fluids that may be subjected to droplet operations using the approach of the present disclosure, see Eckhardt et al., International Patent Pub. No. WO/2007/120241, entitled, "Droplet-Based Biochemistry," published on Oct. 25, 2007, the entire disclosure of which is incorporated herein by reference.

In various embodiments, a droplet may include a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, liquids containing multi-celled organisms, biological swabs and biological washes. Moreover, a droplet may include a reagent, such as water, deionized water, saline solutions, acidic solutions, basic solutions, detergent solutions and/or buffers. A droplet can include nucleic acids, such as DNA, genomic DNA, RNA, mRNA or analogs thereof; nucleotides such as deoxyribonucleotides, ribonucleotides or analogs thereof such as analogs having terminator moieties such as those described in Bentley et al., Nature 456:53-59 (2008); Gormley et al., International Patent Pub. No. WO/2013/131962, entitled, "Improved Methods of Nucleic Acid Sequencing," published on Sep. 12, 2013; Barnes et al., U.S. Pat. No. 7,057,026, entitled "Labelled Nucleotides," issued on Jun. 6, 2006; Kozlov et al., International Patent Pub. No. WO/2008/042067, entitled, "Compositions and Methods for Nucleotide Sequencing," published on Apr. 10, 2008; Rigatti et al., International Patent Pub. No. WO/2013/117595, entitled, "Targeted Enrichment and Amplification of Nucleic Acids on a Support," published on Aug. 15, 2013; Hardin et al., U.S. Pat. No. 7,329,492, entitled "Methods for Real-Time Single Molecule Sequence Determination," issued on Feb. 12, 2008; Hardin et al., U.S. Pat. No. 7,211,414, entitled "Enzymatic Nucleic Acid Synthesis: Compositions and Methods for Altering Monomer Incorporation Fidelity," issued on May 1, 2007; Turner et al., U.S. Pat. No. 7,315,019, entitled "Arrays of Optical Confinements and Uses Thereof," issued on Jan. 1, 2008; Xu et al., U.S. Pat. No. 7,405,281, entitled "Fluorescent Nucleotide Analogs and Uses Therefor," issued on Jul. 29, 2008; and Rank et al., U.S. Patent Pub. No. 20080108082, entitled "Polymerase Enzymes and Reagents for Enhanced Nucleic Acid Sequencing," published on May 8, 2008, the entire disclosures of which are incorporated herein by reference; enzymes such as polymerases, ligases, recombinases, or transposases; binding partners such as antibodies, epitopes, streptavidin, avidin, biotin, lectins or carbohydrates; or other biochemically active molecules. Other examples of droplet contents include reagents, such as a reagent for a biochemical protocol, such as a nucleic acid amplification protocol, an affinity-based assay protocol, an enzymatic assay protocol, a sequencing protocol, and/or a protocol for analyses of biological fluids. A droplet may include one or more beads.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations that are sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to volume of the resulting droplets (i.e., the volume of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading. Droplet operations may be electrode-mediated. In some cases, droplet operations are further facilitated by the use of hydrophilic and/or hydrophobic regions on surfaces and/or by physical obstacles. For examples of droplet operations, see the patents and patent applications cited above under the definition of "droplet actuator." Impedance or capacitance sensing or imaging techniques may sometimes be used to determine or confirm the outcome of a droplet operation. Examples of such techniques are described in Sturmer et al., U.S. Patent Pub. No. 20100194408, entitled "Capacitance Detection in a Droplet Actuator," published on Aug. 5, 2010, the entire disclosure of which is incorporated herein by reference. Generally speaking, the sensing or imaging techniques may be used to confirm the presence or absence of a droplet at a specific electrode. For example, the presence of a dispensed droplet at the destination electrode following a droplet dispensing operation confirms that the droplet dispensing operation was effective. Similarly, the presence of a droplet at a detection spot at an appropriate step in an assay protocol may confirm that a previous set of droplet operations has successfully produced a droplet for detection. Droplet transport time can be quite fast. For example, in various embodiments, transport of a droplet from one electrode to the next may exceed about 1 sec, or about 0.1 sec, or about 0.01 sec, or about 0.001 sec. In one embodiment, the electrode is operated in AC mode but is switched to DC mode for imaging. It is helpful for conducting droplet operations for the footprint area of droplet to be similar to electrowetting area; in other words, 1x-, 2x-3x-droplets are usefully controlled operated using 1, 2, and 3 electrodes, respectively. If the droplet footprint is greater than number of electrodes available for conducting a droplet operation at a given time, the difference between the droplet size and the number of electrodes should typically not be greater than 1; in other words, a 2x droplet is usefully controlled using 1 electrode and a 3x droplet is usefully controlled using 2 electrodes. When droplets include beads, it is useful for droplet size to be equal to the number of electrodes controlling the droplet, e.g., transporting the droplet.

"Filler fluid" means a fluid associated with a droplet operations substrate of a droplet actuator, which fluid is sufficiently immiscible with a droplet phase to render the droplet phase subject to electrode-mediated droplet operations. For example, the droplet operations gap of a droplet actuator is typically filled with a filler fluid. The filler fluid may, for example, be or include low-viscosity oil, such as silicone oil or hexadecane filler fluid. The filler fluid may be or include a halogenated oil, such as a fluorinated or perfluorinated oil. The filler fluid may fill the entire gap of the droplet actuator or may coat one or more surfaces of the droplet actuator. Filler fluids may be conductive or non-conductive. Filler fluids may be selected to improve droplet operations and/or reduce loss of reagent or target substances from droplets, improve formation of microdroplets, reduce cross contamination between droplets, reduce contamination of droplet actuator surfaces, reduce degradation of droplet actuator materials, etc. For example, filler fluids may be selected for compatibility with droplet actuator materials. As an example, fluorinated filler fluids may be usefully employed with fluorinated surface coatings. Fluorinated filler fluids are useful to reduce loss of lipophilic compounds, such as umbelliferone substrates like 6-hexadecanoylamido-4-methylumbelliferone substrates (e.g., for use in Krabbe, Niemann-Pick, or other assays); other umbelliferone substrates are described in Winger et al., U.S. Patent Pub. No. 20110118132, entitled "Enzymatic Assays Using Umbelliferone Substrates with Cyclodextrins in Droplets of Oil," published on May 19, 2011, the entire disclosure of which is incorporated herein by reference. Examples of suitable fluorinated oils include those in the Galden line, such as Galden HT170 (bp=170° C., viscosity=1.8 cSt, density=1.77), Galden HT200 (bp=200C, viscosity=2.4 cSt, d=1.79), Galden HT230 (bp=230C, viscosity=4.4 cSt, d=1.82) (all from Solvay Solexis); those in the Novec line, such as Novec 7500 (bp=128C, viscosity=0.8 cSt, d=1.61), Fluorinert FC-40 (bp=155° C., viscosity=1.8 cSt, d=1.85), Fluorinert FC-43 (bp=174° C., viscosity=2.5 cSt, d=1.86) (both from 3M). In general, selection of perfluorinated filler fluids is based on kinematic viscosity (<7 cSt is preferred, but not required), and on boiling point (>150° C. is preferred, but not required, for use in DNA/RNA-based applications (PCR, etc.)). Filler fluids may, for example, be doped with surfactants or other additives. For example, additives may be selected to improve droplet operations and/or reduce loss of reagent or target substances from droplets, formation of microdroplets, cross contamination between droplets, contamination of droplet actuator surfaces, degradation of droplet actuator materials, etc. Composition of the filler fluid, including surfactant doping, may be selected for performance with reagents used in the specific assay protocols and effective interaction or non-interaction with droplet actuator materials. Examples of filler fluids and filler fluid formulations suitable for use with the methods and apparatus set forth herein are provided in Srinivasan et al, International Patent Pub. No. WO/2010/027894, entitled "Droplet Actuators, Modified Fluids and Methods," published on Jun. 3, 2010; Srinivasan et al, International Patent Pub. No. WO/2009/021173, entitled "Use of Additives for Enhancing Droplet Operations," published on Feb. 12, 2009; Sista et al., International Patent Pub. No. WO/2008/098236, entitled "Droplet Actuator Devices and Methods Employing Magnetic Beads," published on Jan. 15, 2009; and Monroe et al., U.S. Patent Pub. No. 20080283414, entitled "Electrowetting Devices," published on Nov. 20, 2008, the entire disclosures of which are incorporated herein by reference, as well as the other patents and patent applications cited herein. Fluorinated oils may in some cases be doped with fluorinated surfactants, e.g., Zonyl FSO-100 (Sigma-Aldrich) and/or others. A filler fluid is typically a liquid. In some embodiments, a filler gas can be used instead of a liquid.

"Immobilize" with respect to magnetically responsive beads, means that the beads are substantially restrained in position in a droplet or in filler fluid on a droplet actuator. For example, in one embodiment, immobilized beads are sufficiently restrained in position in a droplet to permit execution of a droplet splitting operation, yielding one droplet with substantially all of the beads and one droplet substantially lacking in the beads.

"Magnetically responsive" means responsive to a magnetic field. "Magnetically responsive beads" include or are composed of magnetically responsive materials. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as $Fe_3O_4$, $BaFe_{12}O_{19}$, CoO, NiO, $Mn_2O_3$, $Cr_2O_3$, and CoMnP.

"Reservoir" means an enclosure or partial enclosure configured for holding, storing, or supplying liquid. A droplet actuator system of the present disclosure may include on-cartridge reservoirs and/or off-cartridge reservoirs. On-cartridge reservoirs may be (1) on-actuator reservoirs, which are reservoirs in the droplet operations gap or on the droplet operations surface; (2) off-actuator reservoirs, which are reservoirs on the droplet actuator cartridge, but outside the droplet operations gap, and not in contact with the droplet operations surface; or (3) hybrid reservoirs which have on-actuator regions and off-actuator regions. An example of an off-actuator reservoir is a reservoir in the top substrate. An off-actuator reservoir is typically in fluid communication with an opening or flow path arranged for flowing liquid from the off-actuator reservoir into the droplet operations gap, such as into an on-actuator reservoir. An off-cartridge reservoir may be a reservoir that is not part of the droplet actuator cartridge at all, but which flows liquid to some portion of the droplet actuator cartridge. For example, an off-cartridge reservoir may be part of a system or docking station to which the droplet actuator cartridge is coupled during operation. Similarly, an off-cartridge reservoir may be a reagent storage container or syringe which is used to force fluid into an on-cartridge reservoir or into a droplet operations gap. A system using an off-cartridge reservoir will typically include a fluid passage means whereby liquid may be transferred from the off-cartridge reservoir into an on-cartridge reservoir or into a droplet operations gap.

"Transporting into the magnetic field of a magnet," "transporting towards a magnet," and the like, as used herein to refer to droplets and/or magnetically responsive beads within droplets, is intended to refer to transporting into a region of a magnetic field capable of substantially attracting magnetically responsive beads in the droplet. Similarly, "transporting away from a magnet or magnetic field," "transporting out of the magnetic field of a magnet," and the like, as used herein to refer to droplets and/or magnetically responsive beads within droplets, is intended to refer to transporting away from a region of a magnetic field capable of substantially attracting magnetically responsive beads in the droplet, whether or not the droplet or magnetically responsive beads is completely removed from the magnetic field. It will be appreciated that in any of such cases described herein, the droplet may be transported towards or away from the desired region of the magnetic field, and/or the desired region of the magnetic field may be moved towards or away from the droplet. Reference to an electrode, a droplet, or magnetically responsive beads being "within" or "in" a magnetic field, or the like, is intended to describe a situation in which the electrode is situated in a manner which permits the electrode to transport a droplet into and/or away from a desired region of a magnetic field, or the droplet or magnetically responsive beads is/are situated in a desired region of the magnetic field, in each case where the magnetic field in the desired region is capable of substantially attracting any magnetically responsive beads in the droplet. Similarly, reference to an electrode, a droplet, or magnetically responsive beads being "outside of" or "away from" a magnetic field, and the like, is intended to describe a situation in which the electrode is situated in a manner which permits the electrode to transport a droplet away from a certain region of a magnetic field, or the droplet or magnetically responsive beads is/are situated away from a certain region of the magnetic field, in each case where the magnetic field in such region is not capable of substantially attracting any magnetically responsive beads in the droplet or in which any remaining attraction does not eliminate the effectiveness of droplet operations conducted in the region. In various aspects of the present disclosure, a system, a droplet actuator, or another component of a system may include a magnet, such as one or more permanent magnets (e.g., a single cylindrical or bar magnet or an array of such magnets, such as a Halbach array) or an electromagnet or array of electromagnets, to form a magnetic field for interacting with magnetically responsive beads or other components on chip. Such interactions may, for example, include substantially immobilizing or restraining movement or flow of magnetically responsive beads during storage or in a droplet during a droplet operation or pulling magnetically responsive beads out of a droplet.

"Washing" with respect to washing a bead means reducing the amount and/or concentration of one or more substances in contact with the bead or exposed to the bead from a droplet in contact with the bead. The reduction in the amount and/or concentration of the substance may be partial, substantially complete, or even complete. The substance may be any of a wide variety of substances; examples include target substances for further analysis, and unwanted substances, such as components of a sample, contaminants, and/or excess reagent. In some embodiments, a washing operation begins with a starting droplet in contact with a magnetically responsive bead, where the droplet includes an initial amount and initial concentration of a substance. The washing operation may proceed using a variety of droplet operations. The washing operation may yield a droplet including the magnetically responsive bead, where the droplet has a total amount and/or concentration of the substance which is less than the initial amount and/or concentration of the substance. Examples of suitable washing techniques are described in Pamula et al., U.S. Pat. No. 7,439,014, entitled "Droplet-Based Surface Modification and Washing," issued on Oct. 21, 2008, the entire disclosure of which is incorporated herein by reference.

The terms "top," "bottom," "over," "under," and "on" are used throughout the description with reference to the relative positions of components of the droplet actuator, such as relative positions of top and bottom substrates of the droplet actuator. It will be appreciated that the droplet actuator is functional regardless of its orientation in space.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface. In one example, filler fluid can be considered as a film between such liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

Barcodes and UMIs on Beads

In some embodiments, primers bearing sample barcodes can be immobilized to a solid support. Additionally or alternatively, primers bearing UMI sequences can be immobilized to a solid support. For example, the solid support can be one or more beads. Thus, in certain embodiments, a plurality of beads can be presented, wherein each bead in the plurality bears a unique sample barcode and/or UMI sequence. In some embodiments, individual cells are contacted with one or more beads having a unique set of sample barcodes and/or UMI sequences in order to identify the individual cell. In some embodiments, lysates from individual cells are contacted with one or more beads having a unique set of sample barcodes and/or UMI sequences in order to identify the individual cell lysates. In some embodiments, purified nucleic acid from individual cells are contacted with one or more beads having a unique set of sample barcodes and/or UMI sequences in order to identify the purified nucleic acid from the individual cell. The beads can be manipulated in any suitable manner as is known in the art, for example, using droplet actuators as described hereinabove.

The terms "solid surface," "solid support" and other grammatical equivalents herein refer to any material that is appropriate for or can be modified to be appropriate for the attachment of the primers, barcodes and sequences described herein. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, Teflon™, etc.), polysaccharides, nylon or nitrocellulose, ceramics, resins, silica or silica-based materials including silicon and modified silicon, carbon, metals, inorganic glasses, plastics, optical fiber bundles, and a variety of other polymers. Particularly useful solid supports and solid surfaces for some embodiments are located within a flow cell apparatus. Exemplary flow cells are set forth in further detail below.

In some embodiments, the solid support comprises a patterned surface suitable for immobilization of primers, barcodes and sequences described herein in an ordered pattern. A "patterned surface" refers to an arrangement of different regions in or on an exposed layer of a solid support. For example, one or more of the regions can be features where one or more transposome complexes are present. The features can be separated by interstitial regions where transposome complexes are not present. In some embodiments, the pattern can be an x-y format of features that are in rows and columns. In some embodiments, the pattern can be a repeating arrangement of features and/or interstitial regions. In some embodiments, the pattern can be a random arrangement of features and/or interstitial regions. In some embodiments, the transposome complexes are randomly distributed upon the solid support. In some embodiments, the transposome complexes are distributed on a patterned surface. Exemplary patterned surfaces that can be used in the methods and compositions set forth herein are described in U.S. Ser. No. 13/661,524 or US Pat. App. Publ. No. 2012/0316086 A1, each of which is incorporated herein by reference.

In some embodiments, the solid support comprises an array of wells or depressions in a surface. This may be fabricated as is generally known in the art using a variety of techniques, including, but not limited to, photolithography, stamping techniques, molding techniques and microetching techniques. As will be appreciated by those in the art, the technique used will depend on the composition and shape of the array substrate.

The composition and geometry of the solid support can vary with its use. In some embodiments, the solid support is a planar structure such as a slide, chip, microchip and/or array. As such, the surface of a substrate can be in the form of a planar layer. In some embodiments, the solid support comprises one or more surfaces of a flowcell. The term "flowcell" as used herein refers to a chamber comprising a solid surface across which one or more fluid reagents can be flowed. Examples of flowcells and related fluidic systems and detection platforms that can be readily used in the methods of the present disclosure are described, for example, in Bentley et al., *Nature* 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

In some embodiments, the solid support or its surface is non-planar, such as the inner or outer surface of a tube or vessel. In some embodiments, the solid support comprises microspheres or beads. By "microspheres" or "beads" or "particles" or grammatical equivalents herein is meant small discrete particles. Suitable bead compositions include, but are not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and teflon, as well as any other materials outlined herein for solid supports may all be used. "Microsphere Detection Guide" from Bangs Laboratories, Fishers Ind. is a helpful guide. In certain embodiments, the microspheres are magnetic microspheres or beads.

The beads need not be spherical; irregular particles may be used. Alternatively or additionally, the beads may be porous. The bead sizes range from nanometers, i.e. 100 nm, to millimeters, i.e. 1 mm, with beads from about 0.2 micron to about 200 microns being preferred, and from about 0.5 to about 5 micron being particularly preferred, although in some embodiments smaller or larger beads may be used.

Throughout this application various publications, patents and/or patent applications have been referenced. The disclosure of these publications in their entireties is hereby incorporated by reference in this application.

The term comprising is intended herein to be open-ended, including not only the recited elements, but further encompassing any additional elements.

A number of embodiments have been described. Nevertheless, it will be understood that various modifications may be made. Accordingly, other embodiments are within the scope of the following claims.

What is claimed is:

1. A method of preparing a cDNA library from a plurality of single cells comprising:

releasing mRNA from each single cell to provide a plurality of individual mRNA samples, wherein the mRNA in each individual mRNA sample is from a single cell;

synthesizing a first strand of cDNA from the mRNA in each individual mRNA sample with a first strand synthesis primer mixture, wherein the first strand synthesis primer mixture comprises a mixture of an oligo dT primer and a randomer primer, wherein the oligo dT primer and the randomer primer each comprise a tag to incorporate the tag into the cDNA to provide a plurality of tagged cDNA samples, wherein the cDNA in each tagged cDNA sample is complementary to mRNA from a single cell, and wherein each tag of each tagged cDNA sample has a same first portion comprising a cell-specific identifier sequence, a same first-read sequencing adapter sequence, and a different second portion;

pooling the tagged cDNA samples generated from a plurality of single cells;

amplifying the pooled, tagged cDNA samples to generate pooled, tagged, double-stranded cDNA; and performing a tagmentation reaction on the pooled, tagged, double-stranded cDNA to generate the cDNA library by contacting the pooled, tagged, double-stranded cDNA with a plurality of transposome complexes each comprising a transposase complexed with a transposon comprising a transposon end sequence and a second-read sequencing adapter sequence, wherein the second-read sequencing adapter sequence is different from the first-read sequencing adapter sequence and is identical in all the transposons in the plurality of transposome complexes, wherein the transposome complexes used in the tagmentation reaction do not comprise the first-read sequencing adapter sequence, and wherein the cDNA library comprises a plurality of tagged cDNA fragments having the first-read sequencing adapter sequence on a first strand and the second-read sequencing adapter sequence on a second strand.

2. The method of claim 1, further comprising amplifying the tagged cDNA fragments of the cDNA library to generate amplified, tagged cDNA fragments.

3. The method of claim 2, wherein amplifying the tagged cDNA fragments comprises adding an additional sequence to the 5' end of the amplification products.

4. The method of claim 3, wherein the additional sequence comprises a primer binding sequence for hybridization to a complementary primer binding sequence on a solid support and amplification of the tagged cDNA fragments on the solid support.

5. The method of claim 4, further comprising hybridizing the amplified, tagged cDNA fragments to the complementary primer binding sequence on the solid support, and amplifying the amplified, tagged cDNA fragments on the solid support.

6. The method of claim 5, further comprising sequencing the amplification products on the solid support.

7. The method of claim 1, further comprising sequencing the tagged cDNA fragments of the cDNA library.

8. The method of claim 7, wherein sequencing comprises 3' tag counting.

9. The method of claim 7, wherein sequencing comprises whole transcriptome analysis.

10. The method of claim 1, wherein the first strand synthesis primer mixture comprises a primer comprising a double-stranded portion.

11. The method of claim 10, wherein the first strand synthesis primer mixture reduces concatenation byproducts compared to a single-stranded first strand synthesis primer.

12. The method of claim 10, wherein the first strand synthesis primer mixture comprises a primer comprising a region capable of forming a hairpin.

13. The method of claim 10, wherein the first strand synthesis primer mixture comprises a primer comprising a region of RNA.

14. The method of claim 10, wherein the first strand synthesis primer mixture comprises a primer hybridized to a complementary oligonucleotide, thereby forming a double-stranded portion.

15. The method of claim 1, wherein the tag comprises a unique molecular identifier (UMI) sequence.

16. The method of claim 1, wherein the first strand synthesis primer mixture comprises a primer attached to a bead and the synthesizing comprises synthesizing tagged cDNA samples on the bead.

17. The method of claim 16, comprising encapsulating each single cell in a droplet with the bead before releasing the mRNA from each single cell.

18. The method of claim 17, wherein the releasing and synthesizing of each tagged cDNA sample is performed in the droplet.

19. The method of claim 16, wherein pooling the tagged cDNA samples comprises pooling the beads with the attached tagged cDNA samples.

20. A method of preparing a cDNA library from a plurality of single cells comprising:
    releasing mRNA from each single cell to provide a plurality of individual mRNA samples, wherein the mRNA in each individual mRNA sample is from a single cell;
    synthesizing a first strand of cDNA from the mRNA in each individual mRNA sample with a first strand synthesis primer and incorporating a tag into the cDNA to provide a plurality of tagged cDNA samples, wherein the cDNA in each tagged cDNA sample is complementary to mRNA from a single cell, and wherein the tag comprises a cell-specific identifier sequence, a first-read sequencing adapter sequence, and a unique molecular identifier (UMI) sequence;
    pooling the tagged cDNA samples generated from a plurality of single cells;
    amplifying the pooled cDNA samples to generate pooled, tagged, double-stranded cDNA; and
    performing a tagmentation reaction on the pooled, tagged, double-stranded cDNA to generate the cDNA library by contacting the pooled, tagged, double-stranded cDNA with a plurality of transposome complexes each comprising a transposase complexed with a transposon comprising a transposon end sequence and a second-read sequencing adapter sequence that is identical in all the transposons in the plurality of transposome complexes, wherein the second-read sequencing adapter sequence is different from the first-read sequencing adapter sequence, wherein the transposome complexes used in the tagmentation reaction do not comprise the first-read sequencing adapter sequence, and wherein the cDNA library comprises a plurality of tagged cDNA fragments having the first-read sequencing adapter sequence on a first strand and the second-read sequencing adapter sequence on a second strand.

21. The method of claim 20, further comprising amplifying the tagged cDNA fragments of the cDNA library to generate amplified, tagged cDNA fragments.

22. The method of claim 21, wherein amplifying the tagged cDNA fragments comprises adding an additional sequence to the 5' end of the amplification products.

23. The method of claim 22, wherein the additional sequence comprises a primer binding sequence for hybridization to a complementary primer binding sequence on a solid support and amplification of the tagged cDNA fragments on the solid support.

24. The method of claim 23, further comprising hybridizing the amplified, tagged cDNA fragments to the complementary primer binding sequence on the solid support, and amplifying the amplified, tagged cDNA fragments on the solid support.

25. The method of claim 24, further comprising sequencing the amplification products on the solid support.

26. The method of claim 20, further comprising sequencing the tagged cDNA fragments of the cDNA library.

27. The method of claim 26, wherein sequencing comprises 3' tag counting.

28. The method of claim 20, wherein first strand synthesis is performed using a mixture of random primers, wherein the random primers comprise the tag, optionally wherein the first strand synthesis primer comprises a region capable of forming a hairpin.

29. The method of claim 20, wherein the first strand synthesis primer is hybridized to a complementary oligonucleotide, thereby forming a double-stranded portion.

30. A method of preparing a cDNA library from a plurality of single cells comprising:
    releasing mRNA from each single cell to provide a plurality of individual mRNA samples, wherein the mRNA in each individual mRNA sample is from a single cell;
    synthesizing a first strand of cDNA from the mRNA in each individual mRNA sample with a first strand synthesis primer and incorporating a tag into the cDNA to provide a plurality of tagged cDNA samples, wherein the cDNA in each tagged cDNA sample is complementary to mRNA from a single cell, and wherein the tag comprises a cell-specific identifier sequence and a unique molecular identifier (UMI) sequence, and wherein the first strand synthesis primer comprises:
    (i) a mosaic end region having paired ends and positioned 5' of the UMI sequence, and
    (ii) a first-read sequencing adapter sequence in a hairpin region formed between the paired ends of the mosaic end region;
    pooling the tagged cDNA samples generated from a plurality of single cells;
    amplifying the pooled cDNA samples to generate pooled, tagged, double-stranded cDNA; and
    performing a tagmentation reaction on the pooled, tagged, double-stranded cDNA to generate the cDNA library by contacting the pooled, tagged, double-stranded cDNA with a plurality of transposome complexes each comprising a transposase complexed with a transposon comprising a transposon end sequence and a second-read sequencing adapter sequence that is identical in all the transposons in the plurality of transposome complexes, wherein the second-read sequencing adapter sequence is different from the first-read sequencing adapter sequence, wherein the transposome complexes used in the tagmentation reaction do not comprise the first-read sequencing adapter sequence, and wherein the cDNA library comprises a plurality of tagged cDNA fragments having the first-read sequencing adapter sequence on a first strand and the second-read sequencing adapter sequence on a second strand.

31. The method of claim 30, comprising amplifying the tagged cDNA fragments of the cDNA library to generate amplified, tagged cDNA fragments, wherein amplifying the tagged cDNA fragments comprises adding a primer binding sequence for hybridization to a complementary primer binding sequence on a solid support to the 5' end of the amplification products.

32. The method of claim 31, comprising:
hybridizing the amplified, tagged cDNA fragments to a complementary primer binding sequence on a solid support,
amplifying the amplified, tagged cDNA fragments on the solid support to generate hybridized amplification products, and
sequencing the hybridized amplification products on the solid support.

33. The method of claim 20, wherein the first strand synthesis primer is attached to a bead and the synthesizing comprises synthesizing tagged cDNA samples on the bead.

34. The method of claim 33, comprising encapsulating each single cell in a droplet with the bead before releasing the mRNA from each single cell.

35. The method of claim 34, wherein the droplet is generated using a droplet actuator.

36. The method of claim 34, wherein the releasing and synthesizing of each tagged cDNA sample is performed in the droplet.

37. The method of claim 33, wherein pooling the tagged cDNA samples comprises pooling the beads with the attached tagged cDNA samples.

38. The method of claim 36, wherein pooling the tagged cDNA samples comprises pooling the beads with the attached tagged cDNA samples.

* * * * *

SEQUENCE LISTING

<160> NUMBER OF SEQ ID NOS: 22

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Tn5MEA

<400> SEQUENCE: 1
tcgtcggcag cgtcagatgt gtataagaga cag                                33

<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Tn5MEB

<400> SEQUENCE: 2
gtctcgtggg ctcggagatg tgtataagag acag                               34

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Tn5NTS

<400> SEQUENCE: 3
ctgtctctta tacacatct                                                19

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Random hexamer with P5
<220> FEATURE:
<221> NAME/KEY: modified_base
<222> LOCATION: (30)..(35)
<223> OTHER INFORMATION: n is a, c, g, or t

<400> SEQUENCE: 4
gtgtagatct cggtggtcgc cgtatcattn nnnnn                              35

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Random hexamer with p7 sequence
<220> FEATURE:
<221> NAME/KEY: modified_base
<222> LOCATION: (25)..(30)

<223> OTHER INFORMATION: n is a, c, g, or t

<400> SEQUENCE: 5
atctcgtatg ccgtcttctg cttgnnnnnn                                           30

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Random pentamer + p5
<220> FEATURE:
<221> NAME/KEY: modified_base
<222> LOCATION: (30)..(34)
<223> OTHER INFORMATION: n is a, c, g, or t

<400> SEQUENCE: 6
gtgtagatct cggtggtcgc cgtatcattn nnnn                                      34

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Randomer r7+p5
<220> FEATURE:
<221> NAME/KEY: modified_base
<222> LOCATION: (30)..(36)
<223> OTHER INFORMATION: n is a, c, g, or t

<400> SEQUENCE: 7
gtgtagatct cggtggtcgc cgtatcattn nnnnnn                                    36

<210> SEQ ID NO 8
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Randomer r8+p5
<220> FEATURE:
<221> NAME/KEY: modified_base
<222> LOCATION: (30)..(37)
<223> OTHER INFORMATION: n is a, c, g, or t

<400> SEQUENCE: 8
gtgtagatct cggtggtcgc cgtatcattn nnnnnnn                                   37

<210> SEQ ID NO 9
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Randomer r9+p5
<220> FEATURE:
<221> NAME/KEY: modified_base
<222> LOCATION: (30)..(38)
<223> OTHER INFORMATION: n is a, c, g, or t

<400> SEQUENCE: 9

```
gtgtagatct cggtggtcgc cgtatcattn nnnnnnnn                              38

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Randomer r5+p7
<220> FEATURE:
<221> NAME/KEY: modified_base
<222> LOCATION: (25)..(29)
<223> OTHER INFORMATION: n is a, c, g, or t

<400> SEQUENCE: 10
atctcgtatg ccgtcttctg cttgnnnnn                                         29

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Randomer r&+P7
<220> FEATURE:
<221> NAME/KEY: modified_base
<222> LOCATION: (25)..(31)
<223> OTHER INFORMATION: n is a, c, g, or t

<400> SEQUENCE: 11
atctcgtatg ccgtcttctg cttgnnnnnn n                                      31

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Randomer r8+P7
<220> FEATURE:
<221> NAME/KEY: modified_base
<222> LOCATION: (25)..(32)
<223> OTHER INFORMATION: n is a, c, g, or t

<400> SEQUENCE: 12
atctcgtatg ccgtcttctg cttgnnnnnn nn                                     32

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Randomer r9+p7
<220> FEATURE:
<221> NAME/KEY: modified_base
<222> LOCATION: (25)..(33)
<223> OTHER INFORMATION: n is a, c, g, or t

<400> SEQUENCE: 13
atctcgtatg ccgtcttctg cttgnnnnnn nnn                                    33
```

```
<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aaaaaaaaaa aaaaaaaa                                                       18

<210> SEQ ID NO 15
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tttttttttt tt                                                             12

<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tttttttttt tttttt                                                         16

<210> SEQ ID NO 17
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
aaaaaaaaaa aa                                                             12

<210> SEQ ID NO 18
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
aaaaaaaaaa aaaa                                                           14

<210> SEQ ID NO 19
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tttttttttt ttttt                                                          15
```

```
<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
aaaaaaaaaa aaaaaaaaaa aaaa                                              24

<210> SEQ ID NO 21
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
aaaaaaaaaa aaaaa                                                        15

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tttttttttt tttttttt                                                     18
```